(12) United States Patent
Tarara et al.

(10) Patent No.: US 9,421,166 B2
(45) Date of Patent: *Aug. 23, 2016

(54) PULMONARY DELIVERY OF AMINOGLYCOSIDE

(71) Applicant: NOVARTIS AG, Basel (CH)

(72) Inventors: Thomas E Tarara, Burlinggame, CA (US); Jeffry G Weers, Belmont, CA (US); Maria Geraldine Venthoye, Foster City, CA (US)

(73) Assignee: Novartis AG, Basel (CH)

( * ) Notice: Subject to any disclaimer, the term of this patent is extended or adjusted under 35 U.S.C. 154(b) by 79 days.

This patent is subject to a terminal disclaimer.

(21) Appl. No.: 14/247,546

(22) Filed: Apr. 8, 2014

(65) Prior Publication Data

US 2014/0206638 A1 Jul. 24, 2014

Related U.S. Application Data

(63) Continuation of application No. 11/981,986, filed on Oct. 31, 2007, now Pat. No. 8,715,623, which is a continuation of application No. 10/327,510, filed on Dec. 19, 2002, now Pat. No. 7,368,102.

(60) Provisional application No. 60/342,827, filed on Dec. 19, 2001.

(51) Int. Cl.
| | |
|---|---|
| *A61K 9/12* | (2006.01) |
| *A61K 9/14* | (2006.01) |
| *A61K 31/7036* | (2006.01) |
| *A61K 9/16* | (2006.01) |
| *A61K 9/00* | (2006.01) |

(52) U.S. Cl.
CPC ............ *A61K 9/0075* (2013.01); *A61K 9/1617* (2013.01); *A61K 31/7036* (2013.01)

(58) Field of Classification Search
CPC  A61K 9/0075; A61K 9/1617; A61K 31/7036
See application file for complete search history.

(56) References Cited

U.S. PATENT DOCUMENTS

| | | | |
|---|---|---|---|
| 979,993 A | 10/1910 | O'Byrne et al. | |
| 1,855,591 A | 4/1932 | Wallerstein | |
| 2,457,036 A | 12/1948 | Epstein | |
| 2,797,201 A | 6/1957 | Veatch et al. | |
| 3,014,844 A | 12/1961 | Thiel et al. | |
| 3,362,357 A | 1/1968 | Childs | |
| 3,362,405 A | 1/1968 | Hazel | |
| 3,555,717 A | 1/1971 | Chivers | |
| 3,619,294 A | 11/1971 | Black et al. | |
| 3,655,442 A | 4/1972 | Schwar et al. | |
| 3,745,682 A | 7/1973 | Waldeisen | |
| 3,812,854 A | 5/1974 | Michaels et al. | |
| 3,906,950 A | 9/1975 | Cocozza | |
| 3,948,263 A | 4/1976 | Drake, Jr. et al. | |
| 3,957,964 A | 5/1976 | Grimm, III | |
| 3,964,483 A | 6/1976 | Mathes | |
| 3,975,512 A | 8/1976 | Long, Jr. | |
| 4,009,280 A | 2/1977 | Macarthur et al. | |
| 4,013,075 A | 3/1977 | Cocozza | |
| 4,036,223 A | 7/1977 | Obert | |
| 4,069,819 A | 1/1978 | Valentini et al. | |
| 4,089,120 A | 5/1978 | Kozischek | |
| 4,098,273 A | 7/1978 | Glenn | |
| 4,102,999 A | 7/1978 | Umezawa et al. | |
| 4,127,502 A | 11/1978 | Li Mutti et al. | |
| 4,127,622 A | 11/1978 | Watanabe et al. | |
| 4,158,544 A | 6/1979 | Louderback | |
| 4,159,319 A | 6/1979 | Bachmann et al. | |
| 4,161,516 A | 7/1979 | Bell | |
| 4,180,593 A | 12/1979 | Cohan | |
| 4,201,774 A | 5/1980 | Igarashi et al. | |
| 4,211,769 A | 7/1980 | Okada et al. | |
| 4,244,949 A | 1/1981 | Gupta | |
| 4,253,468 A | 3/1981 | Lehmbeck | |
| 4,281,031 A | 7/1981 | Hillman et al. | |
| 4,326,524 A | 4/1982 | Drake, Jr. et al. | |
| 4,327,076 A | 4/1982 | Puglia et al. | |
| 4,327,077 A | 4/1982 | Puglia et al. | |
| 4,358,442 A | 11/1982 | Wirtz-Peitz et al. | |
| 4,371,557 A | 2/1983 | Oppy et al. | |
| 4,397,799 A | 8/1983 | Edgren et al. | |
| 4,404,228 A | 9/1983 | Cloosterman et al. | |
| 4,407,786 A | 10/1983 | Drake et al. | |

(Continued)

FOREIGN PATENT DOCUMENTS

| | | |
|---|---|---|
| AU | 714998 | 1/1997 |
| AU | 757337 | 2/2003 |
| AU | 731671 | 4/2004 |
| BE | 902257 | 8/1985 |
| CA | 2036844 | 8/1991 |
| CA | 2136704 | 5/1995 |

(Continued)

OTHER PUBLICATIONS

Edwards, A. D., et al. "Crystallization of Pure Anhydrous Polymorphs of Carbamazepine by Solution Enhanced Dispersion with Supercritical Fluids (SEDS™)", *Journal of Pharmaceutical Sciences*, 90(8): 1115-1124 (2001).

Edwards, at al., "Large Porous Particles for Pulmonary Drug Delivery", *Science*, vol. 276, pp. 1868-1871 (Jun. 1997).

Eleutherio, et al., "Role of the Trehalose Carrier in Dehydration Resistance of *Saccharomyces cerevisiae*", *Biochimica et Biophysica Acta*, 1156: 263-266 (1993).

(Continued)

*Primary Examiner* — Mina Haghighatian
(74) *Attorney, Agent, or Firm* — Guy V. Tucker

(57) ABSTRACT

The present invention is directed to the administration of aminoglycosides. In particular, the present invention is directed to compositions and methods for the pulmonary administration of aminoglycosides. According to a preferred embodiment, compositions and methods are provided for the localized treatment of respiratory infections.

19 Claims, 4 Drawing Sheets

(56) References Cited

U.S. PATENT DOCUMENTS

| | | |
|---|---|---|
| 4,452,239 A | 6/1984 | Malem |
| 4,484,577 A | 11/1984 | Sackner et al. |
| 4,524,769 A | 6/1985 | Wetterlin et al. |
| 4,534,343 A | 8/1985 | Nowacki et al. |
| 4,571,334 A | 2/1986 | Yoshida et al. |
| 4,588,744 A | 5/1986 | McHugh |
| 4,590,206 A | 5/1986 | Forrester et al. |
| 4,591,552 A | 5/1986 | Neurath |
| 4,613,500 A | 9/1986 | Suzuki et al. |
| 4,617,272 A | 10/1986 | Kirkwood et al. |
| 4,620,847 A | 11/1986 | Shishov et al. |
| 4,659,696 A | 4/1987 | Hirai et al. |
| 4,667,668 A | 5/1987 | Wetterlin |
| 4,668,218 A | 5/1987 | Virtanen |
| 4,680,027 A | 7/1987 | Parsons et al. |
| 4,684,719 A | 8/1987 | Nishikawa et al. |
| 4,701,417 A | 10/1987 | Portenhauser et al. |
| 4,713,249 A | 12/1987 | Schröder |
| 4,721,709 A | 1/1988 | Seth et al. |
| 4,739,754 A | 4/1988 | Shaner |
| 4,758,583 A | 7/1988 | Cerami et al. |
| 4,761,400 A | 8/1988 | Doat et al. |
| 4,762,857 A | 8/1988 | Bollin, Jr. et al. |
| 4,765,987 A | 8/1988 | Bonte et al. |
| 4,790,824 A | 12/1988 | Morrow et al. |
| 4,793,997 A | 12/1988 | Drake et al. |
| 4,805,811 A | 2/1989 | Wetterlin |
| 4,812,444 A | 3/1989 | Mitsuhashi et al. |
| 4,814,436 A | 3/1989 | Shibata et al. |
| 4,818,542 A | 4/1989 | DeLuca et al. |
| 4,819,629 A | 4/1989 | Jonson |
| 4,824,938 A | 4/1989 | Koyama et al. |
| 4,830,858 A | 5/1989 | Payne et al. |
| 4,847,079 A | 7/1989 | Kwan |
| 4,851,211 A | 7/1989 | Adjei et al. |
| 4,855,326 A | 8/1989 | Fuisz |
| 4,861,627 A | 8/1989 | Mathiowitz et al. |
| 4,865,871 A | 9/1989 | Livesey et al. |
| 4,866,051 A | 9/1989 | Hunt |
| 4,883,762 A | 11/1989 | Hoskins |
| 4,891,319 A | 1/1990 | Roser |
| 4,904,479 A | 2/1990 | Illum |
| 4,906,463 A | 3/1990 | Cleary et al. |
| 4,907,583 A | 3/1990 | Wetterlin et al. |
| 4,942,544 A | 7/1990 | McIntosh et al. |
| 4,950,477 A | 8/1990 | Schmitt et al. |
| 4,952,402 A | 8/1990 | Sparks et al. |
| 4,971,787 A | 11/1990 | Cherukuri et al. |
| 4,984,158 A | 1/1991 | Hillsman |
| 4,988,683 A | 1/1991 | Corbiere |
| 4,995,385 A | 2/1991 | Valentini et al. |
| 4,999,384 A | 3/1991 | Roberts et al. |
| 5,000,591 A | 3/1991 | Burgess |
| 5,006,343 A | 4/1991 | Benson et al. |
| 5,011,678 A | 4/1991 | Wang et al. |
| 5,013,557 A | 5/1991 | Tai |
| 5,017,372 A | 5/1991 | Hastings |
| 5,026,566 A | 6/1991 | Roser |
| 5,026,772 A | 6/1991 | Kobayashi et al. |
| 5,032,585 A | 7/1991 | Lichtenberger |
| 5,033,463 A | 7/1991 | Cocozza |
| 5,043,165 A | 8/1991 | Radhakrishnan |
| 5,049,388 A | 9/1991 | Knight et al. |
| 5,049,389 A | 9/1991 | Radhakrishnan |
| 5,069,936 A | 12/1991 | Yen |
| 5,089,181 A | 2/1992 | Hauser |
| 5,098,893 A | 3/1992 | Franks et al. |
| 5,112,596 A | 5/1992 | Malfroy-Camine |
| 5,112,598 A | 5/1992 | Biesalski |
| 5,118,494 A | 6/1992 | Schultz et al. |
| 5,126,123 A | 6/1992 | Johnson |
| 5,145,684 A | 9/1992 | Liversidge |
| 5,149,543 A | 9/1992 | Cohen et al. |
| 5,149,653 A | 9/1992 | Roser |
| 5,160,745 A | 11/1992 | De Luca et al. |
| 5,173,298 A | 12/1992 | Meadows |
| 5,182,097 A | 1/1993 | Byron et al. |
| 5,190,029 A | 3/1993 | Byron et al. |
| 5,200,399 A | 4/1993 | Wettlaufer et al. |
| 5,202,159 A | 4/1993 | Chen et al. |
| 5,202,333 A | 4/1993 | Berger et al. |
| 5,204,108 A | 4/1993 | Illum |
| 5,208,226 A | 5/1993 | Palmer |
| 5,215,079 A | 6/1993 | Fine et al. |
| 5,225,183 A | 7/1993 | Purewal et al. |
| 5,230,884 A | 7/1993 | Evans et al. |
| 5,239,993 A | 8/1993 | Evans |
| 5,240,712 A | 8/1993 | Smith et al. |
| 5,240,843 A | 8/1993 | Gibson et al. |
| 5,240,846 A | 8/1993 | Collins et al. |
| 5,254,330 A | 10/1993 | Ganderton et al. |
| 5,260,306 A | 11/1993 | Boardman et al. |
| 5,262,405 A | 11/1993 | Girod-Vaquez et al. |
| 5,270,048 A | 12/1993 | Drake |
| 5,284,133 A | 2/1994 | Burns et al. |
| 5,284,656 A | 2/1994 | Platz et al. |
| 5,290,765 A | 3/1994 | Wettlaufer |
| 5,299,566 A | 4/1994 | Davis et al. |
| 5,304,125 A | 4/1994 | Leith |
| 5,306,483 A | 4/1994 | Mautone |
| 5,306,506 A | 4/1994 | Zema et al. |
| 5,308,620 A | 5/1994 | Yen |
| 5,309,900 A | 5/1994 | Knoch et al. |
| 5,312,335 A | 5/1994 | McKinnon et al. |
| 5,312,909 A | 5/1994 | Driessen et al. |
| 5,342,625 A | 8/1994 | Hauer et al. |
| 5,348,730 A | 9/1994 | Greenleaf et al. |
| 5,348,852 A | 9/1994 | Bonderman |
| 5,354,562 A | 10/1994 | Platz et al. |
| 5,354,934 A | 10/1994 | Pitt et al. |
| 5,366,734 A | 11/1994 | Hutchinson |
| 5,376,359 A | 12/1994 | Johnson |
| 5,380,473 A | 1/1995 | Bogue et al. |
| 5,380,519 A | 1/1995 | Schneider et al. |
| 5,384,345 A | 1/1995 | Naton |
| 5,387,431 A | 2/1995 | Fuisz |
| 5,388,572 A | 2/1995 | Mulhauser et al. |
| 5,403,861 A | 4/1995 | Goldin et al. |
| 5,404,871 A | 4/1995 | Goodman et al. |
| 5,422,360 A | 6/1995 | Miyajima et al. |
| 5,422,384 A | 6/1995 | Samuels et al. |
| 5,425,951 A | 6/1995 | Goodrich, Jr. et al. |
| 5,437,272 A | 8/1995 | Fuhrman |
| 5,437,274 A | 8/1995 | Khoobehi et al. |
| 5,451,569 A | 9/1995 | Wong et al. |
| 5,453,514 A | 9/1995 | Niigata et al. |
| 5,458,135 A | 10/1995 | Patton et al. |
| 5,470,885 A | 11/1995 | Fuhrman et al. |
| 5,474,059 A | 12/1995 | Cooper |
| 5,474,759 A | 12/1995 | Fassberg et al. |
| 5,482,927 A | 1/1996 | Maniar et al. |
| 5,490,498 A | 2/1996 | Faithfull et al. |
| 5,492,688 A | 2/1996 | Byron et al. |
| 5,506,203 A | 4/1996 | Backstrom et al. |
| 5,508,269 A | 4/1996 | Smith et al. |
| 5,512,547 A | 4/1996 | Johnson et al. |
| 5,518,709 A | 5/1996 | Sutton et al. |
| 5,518,731 A | 5/1996 | Meadows |
| 5,518,998 A | 5/1996 | Backstrom et al. |
| 5,522,385 A | 6/1996 | Lloyd et al. |
| 5,527,521 A | 6/1996 | Unger et al. |
| 5,540,225 A | 7/1996 | Schutt |
| 5,542,935 A | 8/1996 | Unger et al. |
| 5,547,656 A | 8/1996 | Unger |
| 5,547,696 A | 8/1996 | Sorensen |
| 5,552,160 A | 9/1996 | Liversidge et al. |
| 5,562,608 A | 10/1996 | Sekins et al. |
| 5,567,439 A | 10/1996 | Myers et al. |
| 5,569,448 A | 10/1996 | Wong et al. |
| 5,569,450 A | 10/1996 | Duan et al. |
| 5,571,499 A | 11/1996 | Hafler et al. |
| 5,577,497 A | 11/1996 | Mecikalski et al. |
| 5,580,575 A | 12/1996 | Unger et al. |
| 5,580,859 A | 12/1996 | Felgner et al. |

(56) References Cited

U.S. PATENT DOCUMENTS

| | | |
|---|---|---|
| 5,589,167 A | 12/1996 | Cleland et al. |
| 5,591,453 A | 1/1997 | Ducheyne et al. |
| 5,605,673 A | 2/1997 | Schutt et al. |
| 5,605,674 A | 2/1997 | Purewal et al. |
| 5,607,915 A | 3/1997 | Patton et al. |
| 5,611,344 A | 3/1997 | Bernstein et al. |
| 5,612,053 A | 3/1997 | Baichwal |
| 5,616,311 A | 4/1997 | Yen |
| 5,618,786 A | 4/1997 | Roosdorp et al. |
| 5,621,094 A | 4/1997 | Roser et al. |
| 5,631,225 A | 5/1997 | Sorensen |
| 5,635,159 A | 6/1997 | Fu Lu et al. |
| 5,635,161 A | 6/1997 | Adjei et al. |
| 5,642,728 A | 7/1997 | Andersson et al. |
| 5,648,095 A | 7/1997 | Illum et al. |
| 5,653,961 A | 8/1997 | McNally et al. |
| 5,653,962 A | 8/1997 | Akehurst et al. |
| 5,654,007 A | 8/1997 | Johnson et al. |
| 5,654,278 A | 8/1997 | Sorensen |
| 5,655,521 A | 8/1997 | Faithfull et al. |
| 5,656,297 A | 8/1997 | Bernstein et al. |
| 5,658,549 A | 8/1997 | Akehurst et al. |
| 5,659,297 A | 8/1997 | Tatavoosian |
| 5,667,808 A | 9/1997 | Johnson et al. |
| 5,667,809 A | 9/1997 | Trevino et al. |
| 5,673,686 A | 10/1997 | Villax et al. |
| 5,674,471 A | 10/1997 | Akehurst et al. |
| 5,674,472 A | 10/1997 | Akehurst et al. |
| 5,674,473 A | 10/1997 | Purewal et al. |
| 5,676,929 A | 10/1997 | Akehurst et al. |
| 5,676,931 A | 10/1997 | Adjei et al. |
| 5,681,545 A | 10/1997 | Purewal et al. |
| 5,681,746 A | 10/1997 | Bodner et al. |
| 5,683,676 A | 11/1997 | Akehurst et al. |
| 5,683,677 A | 11/1997 | Purewal et al. |
| 5,688,782 A | 11/1997 | Neale et al. |
| 5,690,954 A | 11/1997 | Illum |
| 5,695,743 A | 12/1997 | Purewal et al. |
| 5,695,744 A | 12/1997 | Neale et al. |
| 5,698,537 A | 12/1997 | Pruss |
| 5,705,482 A | 1/1998 | Christensen et al. |
| 5,707,352 A | 1/1998 | Sekins et al. |
| 5,707,644 A | 1/1998 | Illum |
| 5,718,222 A | 2/1998 | Lloyd et al. |
| 5,718,921 A | 2/1998 | Mathiowitz et al. |
| 5,720,940 A | 2/1998 | Purewal et al. |
| 5,724,957 A | 3/1998 | Rubsamen et al. |
| 5,725,841 A | 3/1998 | Duan et al. |
| 5,725,871 A | 3/1998 | Illum |
| 5,727,546 A | 3/1998 | Clarke et al. |
| 5,728,574 A | 3/1998 | Legg |
| 5,733,555 A | 3/1998 | Chu |
| 5,735,263 A | 4/1998 | Rubsamen et al. |
| 5,736,124 A | 4/1998 | Akehurst et al. |
| 5,740,794 A | 4/1998 | Smith et al. |
| 5,740,970 A | 4/1998 | Edwards |
| 5,741,478 A | 4/1998 | Osborne et al. |
| 5,741,522 A | 4/1998 | Violante et al. |
| 5,743,250 A | 4/1998 | Gonda et al. |
| 5,743,252 A | 4/1998 | Rubsamen et al. |
| 5,744,123 A | 4/1998 | Akehurst et al. |
| 5,744,166 A | 4/1998 | Illum |
| 5,747,001 A | 5/1998 | Wiedmann et al. |
| 5,747,445 A | 5/1998 | Backstrom et al. |
| 5,755,218 A | 5/1998 | Johansson et al. |
| 5,756,104 A | 5/1998 | de Haan et al. |
| 5,766,520 A | 6/1998 | Bronshtein |
| 5,766,573 A | 6/1998 | Purewal et al. |
| 5,770,187 A | 6/1998 | Hasebe et al. |
| 5,770,222 A | 6/1998 | Unger et al. |
| 5,770,559 A | 6/1998 | Manning et al. |
| 5,770,585 A | 6/1998 | Kaufman et al. |
| 5,775,320 A | 7/1998 | Patton et al. |
| 5,776,496 A | 7/1998 | Violante et al. |
| 5,780,014 A | 7/1998 | Eljamal et al. |
| 5,780,295 A | 7/1998 | Livesey et al. |
| 5,785,049 A | 7/1998 | Smith et al. |
| 5,804,212 A | 9/1998 | Illum |
| 5,811,406 A | 9/1998 | Szoka, Jr. et al. |
| 5,814,607 A | 9/1998 | Patton |
| 5,817,293 A | 10/1998 | Akehurst et al. |
| 5,820,883 A | 10/1998 | Tice et al. |
| 5,826,633 A | 10/1998 | Parks et al. |
| 5,829,435 A | 11/1998 | Rubsamen et al. |
| 5,830,430 A | 11/1998 | Unger et al. |
| 5,830,853 A | 11/1998 | Backstrom et al. |
| 5,849,700 A | 12/1998 | Sorensen et al. |
| 5,851,453 A | 12/1998 | Hanna et al. |
| 5,853,698 A | 12/1998 | Straub et al. |
| 5,853,740 A | 12/1998 | Lu et al. |
| 5,853,752 A | 12/1998 | Unger et al. |
| 5,853,763 A | 12/1998 | Tice et al. |
| 5,855,913 A | 1/1999 | Hanes et al. |
| 5,856,367 A | 1/1999 | Barrows et al. |
| 5,858,784 A | 1/1999 | Debs et al. |
| 5,861,175 A | 1/1999 | Walters et al. |
| 5,863,554 A | 1/1999 | Illum |
| 5,873,360 A | 2/1999 | Davies et al. |
| 5,874,063 A | 2/1999 | Briggner et al. |
| 5,874,064 A | 2/1999 | Edwards et al. |
| 5,875,776 A | 3/1999 | Vaghefi |
| 5,891,844 A | 4/1999 | Hafner |
| 5,891,873 A | 4/1999 | Colaco et al. |
| 5,898,028 A | 4/1999 | Jensen et al. |
| 5,921,447 A | 7/1999 | Barger et al. |
| 5,925,334 A | 7/1999 | Rubin et al. |
| 5,928,469 A | 7/1999 | Franks et al. |
| 5,934,273 A | 8/1999 | Andersson et al. |
| 5,948,411 A | 9/1999 | Koyama et al. |
| 5,955,143 A | 9/1999 | Wheatley |
| 5,955,448 A | 9/1999 | Colaco et al. |
| 5,962,424 A | 10/1999 | Hallahan et al. |
| 5,972,366 A | 10/1999 | Haynes et al. |
| 5,972,388 A | 10/1999 | Sakon et al. |
| 5,976,436 A | 11/1999 | Livesley et al. |
| 5,976,574 A | 11/1999 | Gordon |
| 5,985,309 A | 11/1999 | Edwards et al. |
| 5,993,783 A | 11/1999 | Eljamal et al. |
| 5,993,805 A | 11/1999 | Sutton et al. |
| 5,994,314 A | 11/1999 | Eljamal et al. |
| 5,994,318 A | 11/1999 | Gould-Fogerite et al. |
| 5,997,848 A | 12/1999 | Patton |
| 6,001,336 A | 12/1999 | Gordon |
| 6,013,638 A | 1/2000 | Crystal et al. |
| 6,017,310 A | 1/2000 | Johnson et al. |
| 6,019,968 A | 2/2000 | Platz et al. |
| 6,032,666 A | 3/2000 | Davies et al. |
| 6,034,080 A | 3/2000 | Colaco et al. |
| 6,041,777 A | 3/2000 | Faithfull et al. |
| 6,048,546 A | 4/2000 | Sasaki et al. |
| 6,051,256 A | 4/2000 | Platz et al. |
| 6,051,259 A | 4/2000 | Johnson et al. |
| 6,051,566 A | 4/2000 | Bianco |
| 6,060,069 A | 5/2000 | Hill et al. |
| 6,068,600 A | 5/2000 | Johnson et al. |
| 6,071,428 A | 6/2000 | Franks et al. |
| 6,077,543 A | 6/2000 | Gordon et al. |
| 6,086,376 A | 7/2000 | Moussa et al. |
| 6,089,228 A | 7/2000 | Smith et al. |
| 6,113,948 A | 9/2000 | Heath et al. |
| 6,116,237 A | 9/2000 | Schultz et al. |
| 6,117,455 A | 9/2000 | Takada et al. |
| 6,120,751 A | 9/2000 | Unger |
| 6,123,924 A | 9/2000 | Mistry et al. |
| 6,123,936 A | 9/2000 | Platz et al. |
| 6,129,934 A | 10/2000 | Egan et al. |
| 6,136,295 A | 10/2000 | Edwards et al. |
| 6,136,346 A | 10/2000 | Eljamal et al. |
| 6,138,668 A | 10/2000 | Patton et al. |
| 6,139,819 A | 10/2000 | Unger et al. |
| 6,142,216 A | 11/2000 | Lannes |
| 6,143,276 A | 11/2000 | Unger |
| 6,165,463 A | 12/2000 | Platz et al. |
| 6,165,508 A | 12/2000 | Tracy et al. |

(56) References Cited

U.S. PATENT DOCUMENTS

| | | |
|---|---|---|
| 6,165,597 A | 12/2000 | Williams et al. |
| RE37,053 E | 2/2001 | Hanes et al. |
| 6,187,344 B1 | 2/2001 | Eljamal et al. |
| 6,190,859 B1 | 2/2001 | Putnak et al. |
| 6,207,135 B1 | 3/2001 | Rossling et al. |
| 6,230,707 B1 | 5/2001 | Horlin |
| 6,231,851 B1 | 5/2001 | Platz et al. |
| 6,248,720 B1 | 6/2001 | Mathiowitz et al. |
| 6,254,854 B1 | 7/2001 | Edwards et al. |
| 6,257,233 B1 | 7/2001 | Burr et al. |
| 6,258,341 B1 | 7/2001 | Foster et al. |
| 6,284,282 B1 | 9/2001 | Maa et al. |
| 6,290,991 B1 | 9/2001 | Roser et al. |
| 6,303,581 B2 | 10/2001 | Pearlman |
| 6,303,582 B1 | 10/2001 | Eljamal et al. |
| 6,309,623 B1 | 10/2001 | Weers et al. |
| 6,309,671 B1 | 10/2001 | Foster et al. |
| 6,313,102 B1 | 11/2001 | Colaco et al. |
| 6,315,983 B1 | 11/2001 | Eistetter |
| 6,331,310 B1 | 12/2001 | Roser et al. |
| 6,344,182 B1 | 2/2002 | Sutton et al. |
| 6,358,530 B1 | 3/2002 | Eljamal et al. |
| 6,365,190 B1 | 4/2002 | Gordon et al. |
| 6,372,258 B1 | 4/2002 | Platz et al. |
| 6,387,886 B1 | 5/2002 | Montgomery et al. |
| 6,416,739 B1 | 7/2002 | Rogerson et al. |
| 6,423,334 B1 | 7/2002 | Brayden et al. |
| 6,423,344 B1 | 7/2002 | Platz et al. |
| 6,426,210 B1 | 7/2002 | Franks et al. |
| 6,433,040 B1 | 8/2002 | Dellamary et al. |
| 6,468,782 B1 | 10/2002 | Tunnacliffe et al. |
| 6,475,468 B2 | 11/2002 | Zhu et al. |
| 6,479,049 B1 | 11/2002 | Platz et al. |
| 6,503,411 B1 | 1/2003 | Franks et al. |
| 6,503,480 B1 | 1/2003 | Edwards et al. |
| 6,509,006 B1 | 1/2003 | Platz et al. |
| 6,514,482 B1 | 2/2003 | Bartus et al. |
| 6,514,496 B1 | 2/2003 | Platz et al. |
| 6,518,239 B1 | 2/2003 | Kuo et al. |
| 6,551,578 B2 | 4/2003 | Adjei et al. |
| 6,565,871 B2 | 5/2003 | Roser et al. |
| 6,565,885 B1 | 5/2003 | Tarara et al. |
| 6,569,406 B2 | 5/2003 | Stevenson et al. |
| 6,569,458 B1 | 5/2003 | Gombotz et al. |
| 6,572,893 B2 | 6/2003 | Gordon et al. |
| 6,582,728 B1 | 6/2003 | Platz et al. |
| 6,586,006 B2 | 7/2003 | Roser et al. |
| 6,589,560 B2 | 7/2003 | Foster et al. |
| 6,592,904 B2 | 7/2003 | Platz et al. |
| 6,630,169 B1 | 10/2003 | Bot et al. |
| 6,638,495 B2 | 10/2003 | Weers et al. |
| 6,649,911 B2 | 11/2003 | Kawato |
| 6,652,837 B1 | 11/2003 | Edwards et al. |
| 6,655,379 B2 | 12/2003 | Clark et al. |
| 6,673,335 B1 | 1/2004 | Platz et al. |
| 6,681,767 B1 | 1/2004 | Patton et al. |
| 6,685,967 B1 | 2/2004 | Patton et al. |
| 6,737,045 B2 | 5/2004 | Patton et al. |
| 6,737,066 B1 | 5/2004 | Moss |
| 6,752,893 B2 | 6/2004 | Frieder et al. |
| 6,797,258 B2 | 9/2004 | Platz et al. |
| 6,811,792 B2 | 11/2004 | Roser et al. |
| 6,825,031 B2 | 11/2004 | Franks et al. |
| 6,890,907 B2 | 5/2005 | Speirs et al. |
| 6,893,657 B2 | 5/2005 | Roser et al. |
| 6,921,527 B2 | 7/2005 | Platz et al. |
| 6,946,117 B1 | 9/2005 | Schutt et al. |
| 6,946,339 B2 | 9/2005 | Herzum |
| 7,022,311 B1 | 4/2006 | Ohkuma et al. ............... 424/45 |
| 7,306,787 B2 | 12/2007 | Tarara et al. |
| 7,368,102 B2 | 5/2008 | Tarara et al. ............... 424/45 |
| 7,393,544 B2 | 7/2008 | Dellamary et al. |
| 7,442,388 B2 | 10/2008 | Weers et al. |
| 7,790,145 B2 | 9/2010 | Weers et al. ............... 424/46 |
| 8,664,187 B2* | 3/2014 | Challoner ............... A61K 31/70 514/35 |
| 8,715,623 B2* | 5/2014 | Tarara ............... A61K 9/0075 424/45 |
| 2001/0035184 A1 | 11/2001 | Schuler et al. |
| 2002/0017295 A1 | 2/2002 | Weers et al. |
| 2002/0052310 A1 | 5/2002 | Edwards et al. |
| 2002/0127188 A1 | 9/2002 | Platz et al. |
| 2002/0132787 A1 | 9/2002 | Eljamal et al. |
| 2002/0187106 A1 | 12/2002 | Weers et al. |
| 2002/0192164 A1 | 12/2002 | Patton et al. |
| 2003/0035778 A1 | 2/2003 | Platz et al. |
| 2003/0068277 A1 | 4/2003 | Vanbever et al. |
| 2003/0068279 A1 | 4/2003 | Platz et al. |
| 2003/0072718 A1 | 4/2003 | Platz et al. |
| 2003/0086877 A1 | 5/2003 | Platz et al. |
| 2003/0092666 A1 | 5/2003 | Eljamal et al. |
| 2003/0096774 A1 | 5/2003 | Gonda et al. |
| 2003/0113273 A1 | 6/2003 | Patton et al. |
| 2003/0113900 A1 | 6/2003 | Tunnacliff et al. |
| 2003/0143162 A1 | 7/2003 | Speirs et al. |
| 2003/0171282 A1 | 9/2003 | Patton |
| 2003/0185765 A1 | 10/2003 | Platz et al. |
| 2003/0198601 A1 | 10/2003 | Platz et al. |
| 2003/0203036 A1 | 10/2003 | Gordon et al. |
| 2003/0215512 A1 | 11/2003 | Foster et al. |
| 2003/0215514 A1 | 11/2003 | Platz et al. |
| 2003/0219490 A1 | 11/2003 | Hovey et al. |
| 2004/0052825 A1 | 3/2004 | Roser et al. |
| 2004/0096400 A1 | 5/2004 | Patton et al. |
| 2004/0096401 A1 | 5/2004 | Patton et al. |
| 2004/0105820 A1 | 6/2004 | Weers et al. |
| 2004/0156792 A1 | 8/2004 | Tarara et al. |
| 2004/0170568 A1 | 9/2004 | Weers et al. |
| 2004/0219206 A1 | 11/2004 | Roser et al. |
| 2005/0074449 A1 | 4/2005 | Bot et al. |
| 2005/0147566 A1 | 7/2005 | Fleming et al. |
| 2005/0186143 A1 | 8/2005 | Stevenson et al. |
| 2005/0203002 A1 | 9/2005 | Tzannis et al. |
| 2005/0214224 A1 | 9/2005 | Weers et al. |
| 2006/0159625 A1 | 7/2006 | Tarara et al. |
| 2006/0159629 A1 | 7/2006 | Tarara et al. |
| 2006/0165606 A1 | 7/2006 | Tarara et al. |
| 2008/0214481 A1 | 9/2008 | Challoner et al. ............... 514/37 |
| 2012/0148641 A1 | 6/2012 | Challoner et al. ............... 424/400 |

FOREIGN PATENT DOCUMENTS

| | | |
|---|---|---|
| CA | 2421974 A1 | 9/2001 |
| CN | 1493297 A | 5/2004 |
| DE | 0161072 | 10/1904 |
| DE | 471490 | 8/1931 |
| DE | 1080265 | 4/1960 |
| DE | 3141498 | 4/1983 |
| DE | 3713326 | 10/1987 |
| EP | 0282179 | 9/1888 |
| EP | 0015123 | 3/1980 |
| EP | 0072046 | 2/1983 |
| EP | 0090356 | 10/1983 |
| EP | 0111216 | 6/1984 |
| EP | 0129985 | 1/1985 |
| EP | 0136030 | 4/1985 |
| EP | 0139286 | 5/1985 |
| EP | 0140489 | 5/1985 |
| EP | 0222313 | 5/1987 |
| EP | 0229810 | 7/1987 |
| EP | 0274431 | 7/1988 |
| EP | 0325936 | 8/1989 |
| EP | 0356154 | 2/1990 |
| EP | 0360340 | 3/1990 |
| EP | 0391896 | 3/1990 |
| EP | 0366303 | 5/1990 |
| EP | 0372777 | 6/1990 |
| EP | 0383569 | 8/1990 |
| EP | 0415567 | 3/1991 |
| EP | 0430045 | 6/1991 |
| EP | 0433679 | 6/1991 |
| EP | 0463653 | 1/1992 |
| EP | 0467172 | 1/1992 |

(56) References Cited

FOREIGN PATENT DOCUMENTS

| | | |
|---|---|---|
| EP | 0474874 | 3/1992 |
| EP | 0520748 | 10/1992 |
| EP | 0605578 | 1/1994 |
| EP | 0536204 | 4/1994 |
| EP | 0600730 | 8/1994 |
| EP | 0611567 | 8/1994 |
| EP | 0616524 | 9/1994 |
| EP | 0553298 | 11/1994 |
| EP | 0653205 | 5/1995 |
| EP | 0655237 | 5/1995 |
| EP | 0656203 | 6/1995 |
| EP | 0656205 | 6/1995 |
| EP | 0656206 | 6/1995 |
| EP | 0658101 | 6/1995 |
| EP | 0513127 | 7/1995 |
| EP | 0663840 | 7/1995 |
| EP | 0493437 | 8/1995 |
| EP | 0556256 | 8/1995 |
| EP | 0616525 | 9/1995 |
| EP | 0499344 | 10/1995 |
| EP | 0681843 | 11/1995 |
| EP | 0587790 | 1/1996 |
| EP | 0588897 | 2/1996 |
| EP | 0714905 | 6/1996 |
| EP | 07043860 | 11/1996 |
| EP | 0536235 | 1/1997 |
| EP | 0773781 | 5/1997 |
| EP | 0257956 | 3/1998 |
| EP | 0539522 | 12/1998 |
| EP | 0904056 | 3/1999 |
| EP | 1273292 A1 | 1/2003 |
| EP | 1019022 | 4/2003 |
| ES | 84-03520 | 6/1984 |
| FR | 2238476 | 2/1975 |
| GB | 91263780 | 2/1972 |
| GB | 1235615 | 3/1972 |
| GB | 1288094 | 9/1972 |
| GB | 1381588 | 1/1975 |
| GB | 1533012 | 11/1978 |
| GB | 2025196 | 1/1980 |
| GB | 2105189 | 3/1983 |
| GB | 2126588 | 3/1984 |
| GB | 21878191 | 1/1987 |
| GB | 22237510 | 5/1991 |
| GB | 2065659 | 7/1991 |
| GB | 93108753 | 6/1993 |
| GB | 1477775 | 6/1997 |
| JP | 52-139789 | 11/1977 |
| JP | 58-216695 | 12/1983 |
| JP | 59-095885 | 6/1984 |
| JP | 60-244288 | 12/1985 |
| JP | 62-228272 | 10/1987 |
| JP | 62-255434 | 11/1987 |
| JP | 02084401 | 3/1990 |
| JP | 03-038592 | 2/1991 |
| JP | 03264537 | 11/1991 |
| JP | 06-100464 | 4/1994 |
| RU | 91263780 | 12/1991 |
| RU | 92025196 | 6/1992 |
| RU | 93008753 | 5/1993 |
| WO | 86/04095 | 7/1986 |
| WO | 87/00196 | 1/1987 |
| WO | 87/02038 | 4/1987 |
| WO | 87/05300 | 9/1987 |
| WO | 89/06976 | 8/1989 |
| WO | WO8908449 | 9/1989 |
| WO | 90/05182 | 5/1990 |
| WO | 90/11756 | 10/1990 |
| WO | WO9013285 | 11/1990 |
| WO | WO9013328 | 11/1990 |
| WO | 90/15635 | 12/1990 |
| WO | 91/04011 | 4/1991 |
| WO | 91/04715 | 4/1991 |
| WO | 91/06282 | 5/1991 |
| WO | 91/11173 | 8/1991 |
| WO | 91/12823 | 9/1991 |
| WO | 91/16038 | 10/1991 |
| WO | 91/16444 | 10/1991 |
| WO | 91/16882 | 11/1991 |
| WO | 91/18091 | 11/1991 |
| WO | 92/00107 | 1/1992 |
| WO | 92/02133 | 2/1992 |
| WO | 92/11050 | 7/1992 |
| WO | 92/14444 | 9/1992 |
| WO | 92/18164 | 10/1992 |
| WO | 92/19243 | 11/1992 |
| WO | 93/00951 | 1/1993 |
| WO | 93/02834 | 2/1993 |
| WO | 93/09832 | 5/1993 |
| WO | 93/10758 | 6/1993 |
| WO | 93/11744 | 6/1993 |
| WO | 93/11745 | 6/1993 |
| WO | 93/11746 | 6/1993 |
| WO | 93/12240 | 6/1993 |
| WO | WO9311743 | 6/1993 |
| WO | 93/13752 | 7/1993 |
| WO | 93/14172 | 7/1993 |
| WO | 93/17663 | 9/1993 |
| WO | 93/23065 | 11/1993 |
| WO | 93/23110 | 11/1993 |
| WO | 94/04133 | 3/1994 |
| WO | 94/07514 | 4/1994 |
| WO | 94/08552 | 4/1994 |
| WO | 94/08627 | 4/1994 |
| WO | 94/13271 | 6/1994 |
| WO | 94/22423 | 10/1994 |
| WO | 94/24263 | 10/1994 |
| WO | 95/00127 | 1/1995 |
| WO | 95/00128 | 1/1995 |
| WO | 95/01324 | 1/1995 |
| WO | 95/05194 | 2/1995 |
| WO | 95/06126 | 3/1995 |
| WO | WO9509616 | 4/1995 |
| WO | 95/15118 | 6/1995 |
| WO | 95/17195 | 6/1995 |
| WO | 95/20979 | 8/1995 |
| WO | 95/23613 | 9/1995 |
| WO | 95/24183 | 9/1995 |
| WO | 95/24892 | 9/1995 |
| WO | 9527476 | 10/1995 |
| WO | 95/28944 | 11/1995 |
| WO | 95/31182 | 11/1995 |
| WO | 95/31479 | 11/1995 |
| WO | 95/31964 | 11/1995 |
| WO | WO9531964 | 11/1995 |
| WO | 95/33488 | 12/1995 |
| WO | 96/03978 | 2/1996 |
| WO | WO9603116 | 2/1996 |
| WO | 96/09085 | 3/1996 |
| WO | 96/37399 | 3/1996 |
| WO | 96/09814 | 4/1996 |
| WO | WO9607399 | 4/1996 |
| WO | 96/15814 | 5/1996 |
| WO | 96/11745 | 6/1996 |
| WO | 96/18388 | 6/1996 |
| WO | 96/19197 | 6/1996 |
| WO | 96/19198 | 6/1996 |
| WO | 96/19199 | 6/1996 |
| WO | 96/19968 | 7/1996 |
| WO | 96/26746 | 9/1996 |
| WO | 96/27393 | 9/1996 |
| WO | 96/32096 | 10/1996 |
| WO | 96/32149 | 10/1996 |
| WO | WO9632116 | 10/1996 |
| WO | WO9636314 | 11/1996 |
| WO | 96/40049 | 12/1996 |
| WO | 96/40068 | 12/1996 |
| WO | 96/40077 | 12/1996 |
| WO | 96/40277 | 12/1996 |
| WO | WO9640285 | 12/1996 |
| WO | 97/03649 | 2/1997 |
| WO | WO9713503 | 4/1997 |
| WO | 97/26863 | 7/1997 |
| WO | WO9725086 | 7/1997 |

(56) References Cited

FOREIGN PATENT DOCUMENTS

| | | |
|---|---|---|
| WO | 97/34689 | 9/1997 |
| WO | WO9732609 | 9/1997 |
| WO | 97/35562 | 10/1997 |
| WO | 97/36574 | 10/1997 |
| WO | 97/36578 | 10/1997 |
| WO | 97/40819 | 11/1997 |
| WO | 97/41833 | 11/1997 |
| WO | 97/44012 | 11/1997 |
| WO | 97/44013 | 11/1997 |
| WO | 98/00111 | 1/1998 |
| WO | 98/01161 | 1/1998 |
| WO | 98/05302 | 2/1998 |
| WO | 98/07414 | 2/1998 |
| WO | 98/08519 | 3/1998 |
| WO | WO9808519 | 3/1998 |
| WO | 98/13031 | 4/1998 |
| WO | 98/16205 | 4/1998 |
| WO | 98/17257 | 4/1998 |
| WO | 98/24882 | 6/1998 |
| WO | 98/29097 | 7/1998 |
| WO | 98/29098 | 7/1998 |
| WO | 98/29099 | 7/1998 |
| WO | 98/29140 | 7/1998 |
| WO | 98/30207 | 7/1998 |
| WO | 98/31346 | 7/1998 |
| WO | WO9829096 | 7/1998 |
| WO | 98/33480 | 8/1998 |
| WO | 98/33487 | 8/1998 |
| WO | 98/41188 | 9/1998 |
| WO | 88/08/298 | 11/1998 |
| WO | WO9851282 | 11/1998 |
| WO | 98/58989 | 12/1998 |
| WO | 99/06026 | 2/1999 |
| WO | 99/16419 | 4/1999 |
| WO | 99/16420 | 4/1999 |
| WO | 99/16421 | 4/1999 |
| WO | 99/16422 | 4/1999 |
| WO | 99/32083 | 7/1999 |
| WO | 99/32098 | 7/1999 |
| WO | 99/38493 | 8/1999 |
| WO | WO9945986 | 9/1999 |
| WO | WO9945987 | 9/1999 |
| WO | WO9947196 | 9/1999 |
| WO | 99/66903 | 12/1999 |
| WO | WO9966903 | 12/1999 |
| WO | 00/00176 | 1/2000 |
| WO | 00/10541 | 3/2000 |
| WO | 00/21594 | 4/2000 |
| WO | 00/00215 | 6/2000 |
| WO | WO0035461 | 6/2000 |
| WO | 00/72904 | 12/2000 |
| WO | 01/00263 | 1/2001 |
| WO | 01/13892 | 3/2001 |
| WO | 0113891 A2 | 3/2001 |
| WO | 0113893 A2 | 3/2001 |
| WO | 01/32144 | 5/2001 |
| WO | 01/85136 | 11/2001 |
| WO | 01/87278 | 11/2001 |
| WO | 0185137 A2 | 11/2001 |
| WO | WO 0185136 * | 11/2001 |
| WO | 01/95874 | 12/2001 |
| WO | 03005411 A2 | 1/2003 |
| WO | 03041776 A1 | 5/2003 |
| WO | 03041777 A1 | 5/2003 |
| WO | 03057593 A1 | 7/2003 |
| WO | 03094890 A1 | 11/2003 |
| WO | WO2006002140 | 1/2006 |

OTHER PUBLICATIONS

Fahy, et al., "Vitrification as an Approach to Cryopresemation", *Cryobiology*, 21: 407-426 (1984).

Finer, I.L., §14. Trehalose, m.p. 203° C°, under "Carbohydrate" Organic Chemistry, vol. 2, Stereochemistry and the Chemistry of Natural Products, 5th edition, Longman, p. 323 (1996).

Forbes, R.T., et al., "Water Vapor Sorption Studies on the Physical Stability of a Series of Spray-Dried Protein/Sugar Powders for Inhalation", *Journal of Pharmaceutical Sciences*, 87(11): 1316-1321 (1998).

Franks, "Freeze Drying: From Empiricism to Predictability", *Cyro-Letters*, 11: 93-110 (1990).

Franks, "Materials Science and the Production of Shelf-Stable Biologicals", *Pharmaceutical Technological International*, 24: 24-34 (Oct. 1991).

Franks, "Separation, Improved Freeze-Drying, an Analysis of the Basic Scientific Principles", *Process Biochemistry*, 24(1): iii-vii (1989).

Franks, "Accelerated Stability Testing of Bioproducts: Attractions and Pitfalls", *TIBTECH*, 12: 114-117 (1994).

French, Donna L., et al., "The Influence of Formulation on Emission, Deaggregation and Deposition of Dry Powders for Inhalation," *J. Aerosol Science*, vol. 27, No. 5, pp. 769-783 (1996).

Chapter 89—Oral Solid Dosage Forms, In *Remington's Pharmaceutical Sciences*, 18th Edition, Mack Publishing Co., Gennaro, A.R., pp. 1646-1647.

Green, et al., "The Protein-Glass Analogy: Some insights from Homopeptide Comparisons", *J. Phys. Chem.*, 98: 13780-13790 (Apr. 1994).

Green, et al., "Phase Relations and Vitrification in Saccharide-Water Solutions and the Trehalose Anomaly", *J. Phys. Chem.*, 93: 2880-2882 (1989).

Hahn, et al., "Solid Surfactant Solutions of Active Ingredients in Sugar Esters", *Pharmaceutical Research*, 6: 958-959 (1989).

Hancock, et al., "The Use of Solution Theories for Predicting Water Vapor Absorption by Amorphous Pharmaceutical Solids: A Test of the Flory-Huggins and Vrentas Models", *Pharmaceutical Research*, 10(9): 1262-1267 (1993).

Hancock, et al., "Molecular Mobility of Amorphous Pharmaceutical Solids Below Their Glass Transition Temperatures", *Pharmaceutical Research*, 12(6): 799-806 (1995).

Hancock, B.C., et al., "The Effect of Temperature on Water Vapor Sorption by Some Amorphous Pharmaceutical Sugars", *Pharmaceutical Development and Technology*, 4(1): 125-131 (1999).

Hanes, et al., "Porous Dry-Powder PLGA Microspheres coated with Lung Surfactant for Systematic Insulin Delivery via the Lung", *Proc. Int'l. Symp. Control Rel. Bioactive Matter*, 24: 57-58 (1997).

Harwood, C.F., "Compaction Effect on Flow Property Indexes for Powders", *J. Pharm. Sci.*, 60:161-163 (1971).

Hatley, R.H.M., et al., "Stabilization of Labile Materials by Amorphous Carbohydrates Glass Fragility and the Physiochemcial Properties that make Trehalose a Superior Excipient", *Pharamceutical Research*, 13(9 Suppl.) PDD 7165: S274 (1996).

Heitefuss, R., et al., "The Stabilization of Extract of Cabbage Leaf Proteins by Polyhydroxy Compounds for Electrophorectic and Immunological Studies", Archives of *Biochemistry and Biophysics*, 85: 200-208 (1959).

Heller, Martin C., et al., *Protein Formulation and Lyophilization Cycle Design: Prevention of Damage Due to Freeze-Concentration Induced Phase Separation* 63 Biotechnology & Bioengineeting, 166-174 (1999).

Herrington, T.M., "Physico-Chemical Studies on Sugar Glasses. I. Rates of Crystallization", *Journal of Food Technology*, 19: 409-425 (1984).

Hickey, A. J. et al., "Behavior of Hygroscopic Pharmaceutical Aerosols and the Influence of Hydrophobic Additives," *Pharmaceutical Research* 10(1):1-7 (1993).

Hickey, A. J. et al., "Methods of Aerosol Particle Size Characterization," *Pharmaceutical Inhalation Aerosol Technology* 8:219-253 (1992).

Hoener, Betty-Ann et al., "Factors Influencing Drug Absorption and Availability" *Modern Pharmaceutics*, Gilber S. Banker et al., eds., Marcel Dekker Inc., Chapter 4, pp. 121-153 (1996).

Igaki, N. et al., "The Inhibition of the Mailard Reaction by L Lysine In-Vitro," *J. Jpn. Diabetes Soc.* 34(5):403-407 (1991) including English abstract.

Jovanovic-Peterson, L. et al., "Jet-injected insulin is associated with decreased antibody production and postprandial glucuose variability

(56) References Cited

OTHER PUBLICATIONS when compared with needle injected insulin in gestational diabetic women," *Diabetes Care* 16(11):1479-1484 (Nov. 1993).

Kachura, "Method of Drying Lactic Acid Bacteria," Vinodelie I Vinogradarstvo SSSR 2:49-50, English Abstract only, one page. (1985).

Kenna, K. et al., "Denaturation of Fish Muscle Protein by Dehydration" *Bull. Tokai Reg. Fish. Res. Lab.* 77:70-76 English abstract (1974).

Karmas. R. at at, "Effect of Glass Transition on Rates of Nonenzymatic Browning in Food Systems," *J. Agric. Food Chem.* 40:873-879 (1992).

Khan, R. "Chemistry And New Uses Of Sucrose: How Important?" *Pure & Appl. Chem.* 56(7):833-844 1984.

Khan, R "Cyclic Acetals Of 4,1',6'-Tricholoro-4,1',6'-Trideoxy-Galacto-Sucrose And Their Conversion Into Methyl Ether Derivatives," *Carb. Res.* 198:275-283 (1990).

Klein, T. M. et al,, "High Velocity Microprojectiles For Delivering Nucleic Acids Into Living Cells," *Nature* 327:70-73 (1987).

Labuza el al, "Glass Transition Temperatures of Food Systems", [on-line] [retrieved Sep. 2005] Retrieved from the Internet <URL: http://faculty.che.umn.edu/fscn/TedLebuza/PDF_files/Isotherm_Folder/Tg%20compilation.pdf> pp. 1-31 (Jan. 1992).

Labrude, P. et al., "Protective Effect of Sucrose on Spray Drying of Ocxyhemoglobin," *Journal of Pharmaceutical Sciences.* 78(3):223-229 (1989).

Lai, M. C. et al., "Solid-State Chemical Stability of Proteins and Peptides", *Journal of Pharmaceutical Sciences* 88(5):489-500 (1999).

Laube, B. L. et al., "Targeting Aerosol Deposition in Patients With Cystic Fibrosis, Effects of Alterations in Particle Size and Inspiratory Flow Rate", *Chest* 118(4): 1069-1076 (2000).

Led, F., et al., "New Aspects of the Maillard Reaction in Foods and in the Human Body," *Ang. Chem. Int. Ed.* Engl. 29:565-594 (Jun. 1990).

Lee, C. K. *Developments in Food Carbohydrate*—2nd edition Applied Science Publishers, London, Table of Contents, 4 pages (1980).

Lettninger, Albert L. *The Molecular Basis of Call Structum and Function* Biochemistry, Chapter 31 859-890 (Worth Publishers Inc., 2nd edition, 1975).

Leslie, S. B. et al., "Trehalose and sucrose protect both membranes and proteins in intact bacteria during drying", *Appl. Env. Microbiol.* 61(10): 3592-3597 (1995).

Leuner, C. et al., "Improving Drug Solubility for Oral Delivery Using Solid Dispersions", *European Journal of Pharmaceutics and Biopharmaceutics* 50:47-60 (2000).

Levine et al., "Another View of Trehalose for Dying and Stabilizing Biological Materials," *Biopharm* 5:36-40 (1992).

Louis, P. et al., "Survival Of *Escherichia coli* During Drying And Storage In The Presence of Compatible Solutes" *Appl. Microbiol. Biotechnol.* 41:684-688 (1994).

Lueckel, B. et al., "Effects of Formulation and Process Variables on the Aggregation of Freeze-Dried Interleukin-6 (IL-6) After Lyophilization and on Storage", *Pharmaceutical Development end Technology* 3(3):337-346 (1998).

Masinde, Lwandiko E., et al., "Aerosolized Aqueous Suspension of Poly(L-lactic Acid) Microspheres,", *100 International Journal of Pharmaceutics*, pp. 123-131 (1993).

MacKenzie, "Collapse During Freeze Drying-Qualitative and Quantitative Aspects." *Freeze Drying and Advanced Food Technology*, edited by Goldblith, Rey and Rothmayr: 277-307 (1975).

Makower, B. et al., "Equilibrium Moisture Content and Crystallization of Amorphous Sucrose and Glucose," *Agric. And Food Chem.* 4(I):72-77 1956.

Martin, A. et al., States of Matter and Phase Equilibria Physical Pharmacy, Physical Chemical Principles in the Pharmaceutical Sciences. 3rd. ed., Chapter 4, 62-92 (1983).

Matsuda, Y. et al., "Amorphism and Physicochemical Stability of Spray Dried Frusemide," *J. Pharm. Pharmacol.* 44:627-633, received Nov. 7, 1991 (1992).

Mattern et al., "Formulation of Proteins in Vacuum-Dried Glasses. II. Process end Storage Stability in Sugar-Free Amino Acid Systems", *Pharmaceutical Development & Technology* 4(2):199-208 (1999).

Miller, D. P. et al., "Stabilization of Lactate Dehydrogenase Following Freeze Thawing and Vacuum-Drying in the Presence of Trehalose and Borate", *Pharmaceutical Research* 15(8):1215-1221(1998).

Monnier et al., *Mechanisms of Protection Against Damage Mediated by the Maiilard Reaction in Aging Gerontology* 37:152-165 (1991).

Mouradian, R. et al., "Degradation of Functional Integrity During Long-Term. Storage of a Freeze-Dried Biological Membrane", *Cryobiology* 22: 119-127 (1985).

Moynihan et al., "Dependence of the Glass Transition temperature on Heating and Cooling Rate", *J. Physical. Chem.* 78(26): 2673-2677 (1974).

Muller, et al., "On the Influence of Molecular Forces on the Deformation of an Elastic Sphere and It's Sticking to a Rigid Plane", *J. Colloid Interface Sci.*, 77: 91 (1080).

Mumenthaler, M. et al., "Feasibility Study on Spray-Drying Protein Pharmaceuticals: Recombinant Human Growth Hormone and Tissue-Type Plasminogen Activator," *Clinical Research* 11(I): 12-20 (1994).

Murphy, Brian R. et al., *Fields Virology*, vol. 1, Chapter 16, *Immunization Against Virus Disease*, 467, at p. 468, first full paragraph, first column, lines 26-33 (Bernard N. Field et al. eds., Lippincott-Raven Publishers, 3rd ed. 1996).

Nabel. G. J. at al., "Direct Gene Transfer With DNA-Liposome, Complexes in Melanoma," Proc. National Academy of Science. 90:11307-11311.

Nabel, G. J. et al., "Immunotherapy of Malignancy by In Vivo Gene Transfer Into Tumors," *Hum. Gene. Ther.* 3(4): 3 99-4 10 (Aug. 1992) Abstract only [on-line] [retrieved 112/21/04] Retrieved from the Internet <URL: http://www.ncbi.nlm.nih.gov/entrez/query.fcgi?cmd=Retrieve&db=pubmed&dopt=Abstr>.

Naini, V. et al., "Particles for Inhalation Produced by Spray Drying and Electrostatic Precipitation of Different Protein-Sugar Solutions", *Respiratory Drug Delivery V*, pp. 382-384 (1996).

Naini, V. et al., "Physicochemcial Stability of Crystalline Sugars and Their Spray-Dried Forms: Dependence Upon Relative Humidity and Suitability for Use in Powder Inhalers", *Drug Development and Industrial Pharmacy* 24(10):895-909 (1998).

Niven, R, W., "Delivery of Biotherapeutics by Inhalation Aerosols," *Pharmaceutical Technology* 72-75, 80 (Jul. 1993).

Norberg, J. et al., "Glass Transition in DNA From Molecular Dynamics Simulation", *Proc. Natl. Acad. Sci. USA* 93:10173-10176 (1996).

Notter, R.H., "Physical Chemistry and Physiological Activity of Pulmonary Surfactants", In: Surfactant Replacement Therapy (Eds. Shapiro and Notter, Alan R. Liss, Inc., New York), Chapter 2, pp. 19-71 (1989).

Oksanen et al, "The Relationship between the Glass Transition Temperature and Water Vapor Absorption by Poly(Vinylpyrrodlidone)," *Pharmaceutical Research* 7(6): 654-657 and errata on p. 974(1990).

Okumura, K. et al., "Intracheal Delivery of Calcitonin Dry Powder in Rats and Human Volunteers," *S.T.P. Pharmceutical Sciences* 4(I):5 pages (Jan. Feb. 1994).

Onodera et al., "Glass Transition of Dehyrdated Amorphous Solid", *Bull. Chem. Soc. Japan* 41(9):222 (1968).

Palmer, K.J., et al., "X-Ray Diffractometer and Microscopic Investigation of Crystallization of Amorphous Sucrose", *Agricultural and Food Chemistry* 4(1): 77-81 (Jan. 1956).

Parks, "Studies on Glass. II The Transition Between the Glassy and Liquid States in the Case of Glucose", *Journal of Physical Chemistry* 1366-1379 (1928).

Pekarek et al., "Double-walled polymer microspheres for controlled drug release," *Nature* 367:258-260 (1994).

Pikal, M. J., "Freeze-Drying of Proteins Part II: Formulation Selections," *Biopharm* 3(8):26-30 (Oct. 1990).

Pikal, M. et al., "The Stability of Insulin in Crystalline and Amorphous Solids: Observation of Greater Stability for the Amorphous Form", *Pharmaceutical Research* 14(10):1379-1387 (1997).

Pikal et al., "Thermal Decomposition of Amorphous β-Lactam Antibacterials", *Journal of Pharmaceutical Science* 66(9): 1312-1316 (Sep. 1977).

(56) References Cited

OTHER PUBLICATIONS

Pine, S. H. et al., "15-3 Oligosaccharides and Polysaccharides," *Organic Chemistry*, 4a' edition. McGraw-Hill International Book Company, p. 763 (1980).
Pisecky, J., "2. Evaporation and Membrane Filtration", *Handbook of Milk Powder Manufacture*, Niro A/S, Denmark, p. 3 (1997).
Pocchiari, M. et al., "Amphotericin B: A Novel Class of Antiscrapie Drugs," *J Infect. Dis.* 16(5):795-802 (Nov. 1989).
Prestrelski, S. J. el al., "Optimization of Lyophilization Conditions for Recombinant Human Interleukin-2 by Dried-State Confonmgonal Analysis Using Fourier-Transform Infrared Spectroscopy," *Pharmaceutical Research* 12(9):1250-1259 (1995).
Prestrelski, S. J. at al , "Separation of Freezing- and Drying-Induced Denaturation of Lyophilized Proteins Using Stress-Specific Stabilization," *Archives of Biochemistry and Biophysics* 303(2 :465-473 (Jun. 1993).
Quart. C. *Protein Science* 4(2):148, Abstract No. 490-T (1995).
Ramanujam, R. et al., "Ambient-Temperature-Stable Molecular Biology Reagents," *Biotechniques* 14(3):470-473 (1993).
Roos, "Phase Transitions of Mixtures of Amorphous Polysaccharides and Sugars," *Biotechnology Progress* 7(I): 49-53 (1991).
Roser, et al., "A Sweeter Way To Fresher Food" *New Scientist* pp. 25-28 (May 15, 1993).
Roser, B., "Trehalose, A New Approach to Premium Dried Foods," *Trends in Food Sci. and Tech.* pp. 166-169 (Jul. 1991).
Roser, B., "Trehalose Drying: A Novel Replacement For Freeze Drying" *Biopharm* 4:47-53 (1991).
Sacchetti, et al., "Spray-Drying and Supercritical Fluid Particle Generation Techniques", *Inhalation Aerosols: Physical and Biological Basis for Therapy*, A.J. Hickey, ed., Marcel Dekker, New York, Chapter 11, p. 337 (1996).
Saleki-Gerhardt, A. et al., "Non-Isothermal and Isothermal Crystallization of Sucrose From the Amorphous State," *Pharmaceutical Research* 11 (8):1166-1173 (1994).
Saleki-Gerhardt, A. et al., "Hydration and Dehydration of Crystalline and Amorphous : Forms of Raffinose," *Journal of Pharmaceutical Sciences*, 84(3):318-323 (Mar. 1995).
Sambrook, et al., *Molecular Cloning: A Laboratory Manual*, 2nd. ed., "Concentrating Nucleic Acids: Precipitation with Ethynol or Isopropanol", pp. E.10-E.17, Cold Spring Laboratory (1989).
Sanchez, J. at al., "Recombinant System for Overexpression of Cholera Toxin B Subunit In Vibrio Cholerae as a Basis for Vaccine Development" *Proc. Natl. Acad. Sci.* USA 86: 481-485 (1989).
Sarkar and Moore, "Immunization of Mice Against Murine Mammary Tumor Virus Infection and Mammary Tumor Development," *Cancer Research* 38:1468-1472 (1978).
Schamblin and Zografi. "Enthalpy Relaxation in Binary Amorphous Mixtures Containing Sucrose", *Pharmaceutical Research* 15(12): 1828-1834 (Dec. 1998).
Schebor, C. et al., "Color Formation Due to Non-Enzymatic Browning in Amorphous, Glassy, Anhydrous, Model Systems", *Food Chemistry* 65:427432 (1999).
Sebhatu, T. et al., "Assessment of the Degree of Disorder in Crystalline Solids by Isothermal Microcalorimetry," *International Journal of Pharmaceutics* 104:135-144 (1994).
Sellers, S. P. et al., "Dry Powders of Stable Protein Formulations From Aqueous Solutions Prepared Using Supercritical C02-Assisted Aerosolization", *Journal of Pharmaceutical Sciences*, 90(6): 785-797 (2001).
Serajuddin, A. T. M. et al., "Effect of Thermal History on the Glassy State of Indapamide," *J. Pharm. Pharmacol.* 38:219-200 (1986).
Shalaev, E.Y. et al., "How Does Residual Water Affect The Solid-State Degradation of Drugs in the Amorphous State", *Journal of Pharmaceutical Sciences*, 85(11): 1137-111 (1996).
Shalaev, E.Y. et al., "Structural Glass Transitions and Thermophysical Processes in Amorphous Carbohydrates and Their Supersaturated Solutions," *J. Chem. Soc. Faraday Trans.* 91(10):1511-1517 (1995).
Simha et al., "On a General Relation Involving the Glass Temperature and Coefficients of Expansion of Polymers", *J. Chem. Physics*, 37(5):1003.

Singer et al., "Thermotolerance in *Saccharomyces cerevisiae*: the Yin and Yang of Trehalose", *Tibtech* 16:460-468. (1998).
Skrabanja et al., "Lyophilization of Biotechnology Products" *PDA J. Pharm. Sci. Technol.* 48(6):311.
Slade and Levine, "Non-Equilibrium Behavior of Small Carbohydrate-Water Systems," *Pure and Applied Chemistry*, 60(12): 1841-1864 (1988).
Sokolov at al., "Gassy Dynamics in DNA: Ruled by Water of Hydration" *Journal of Chemical Physics* 110(14):7053-7057 (1999).
Sola-Penna, Mauro et al., *Stabilization Against Thermal Inactivation Promoted by Sugars on Enzyme Structure and Function: Why is Trehalose More Effective Than Other Sugars?* 360(I) Archives of Biochemistry and Biophysics 10-14, Article No. BB9809606, (Dec. 1998).
Stribling, R. et al., "Aerosol Gene Delivery in Vivo," *Proc. Natl. Acad. Sci.* 89:11277-11281 (Dec. 1992).
Strickley, R. G. et al., "Solid-State Stability of Human Insulin II. Effect of Water on Reactive Intermediate Partitioning in Lyophiles from pH 2-5 Solutions: Stabilization Against Covalent Dimer Formation", *Journal of Pharmaceutical Sciences* 86(6):645-653 (1997).
Strom, A. R. and Kaasen. L. "Trehalose Metabolism in *Escherichia coli*: Stress Protection and Stress Regulation of Gene Expression", *Molecular Microbiology* 8(2):205-210 (1993).
Stubberud, L. et al., "The Use of Gravimetry for the Study of the Effect of Additives on the Moisture-Induced Recrystallisation of Amorphous State", *International Journal of Pharmaceutics* 163:145-156 (1998).
Sukenik at al., "Enhancement of a Chemical Reaction Rate by Proper Orientation of Reacting Molecules in the Solid State," *J. Am. Chem. Soc.* 97: 5290-5291 (Sep. 1975).
Takahashi at at., "Induction of CD8+ cytotoxic T cells by immunization with purified HIV-1 envelope protein in ISCOMs", *Nature* 344:873-875 (Apr. 1990).
Tarara, Thomas, et al., "Characterization of Suspension-Based Metered Dose Inhaler Formulations Composed of Spray-Dried Budesonide Microcrystals Dispersed in HFA-134a," *Pharmaceutical Research*, vol. 21, No, 9: pp. 1607-1614, (Sep. 2004).
Tarelli, E. et al., "Additives to Biological Substances. 111. The Moisture Content and Moisture Uptake of Commonly Used Carrier Agents Undergoing Processing Conditions Similar to Those Used in the Preparation of International Biological Standards," *Journal of Biological Standardization* 15: pp. 331-340, (1987).
Timko et al., "Thermal Analysis Studies of Glass Dispersion Systems", *Drug Devel. Ind. Pharm.* 10:425-451 (1984).
Timsina, T. et al., "Drug Delivery to the Respiratory Tract Using Dry Powder Inhalers," *International Journal of Pharmaceutics* 101:1-13 (1994).
Toyama, A. (ed) *Handbook of Natural Product for food processing*, 9th Edition, Osaka, Japan, Shokuhin to Kagaku Sha, pp. 384 and 495 (ISBN4-87994-048-8),(1986).
Tsouroufflis, S. et al., "Loss of Structure in Freeze-Dried Carbohydrates Solutions: Effect of Temperature, Moisture Content and Composition," *J. Scl. Fd. Agric.* 27:509 519 (1976).
Underwood et al., "A Novel Technique for the Administration of Bronchodilator Drugs Formulated as Dry Powders to the Anaesthetized Guinea Pig", *J. of Pharmacological Methods*, vol. 26, pp. 203-210, 1991.
Uritani, M. et al., "Protective Effect of Disaccharides on Restriction Endonucleases During Drying Under Vacuum." *J. Biochem.* 117:774-779 (1995).
Vain et al., "Development of the particle inflow gun", *Plant Cell, Tissue and Organ Culture* 33:237-246 (1993).
Vavelyuk, O.L. et al., "Thermostability of DNA and Its Association with Vitrification", *Tsitologiya* 41(11):958-965 (1999).
Vidgrén, M. T. et al., "Comparison of Physical and Inhalation Properties of Spray-Dried and Mechanically Micronized Disodium Cromoglycate," *International Journal of Pharmaceutics* 35:139-144 (1987).
Vromans, H. et al,, "Studies on Tableting Properties of Lactose. VII. The Effect of Variations in Primary Particle Size and Percentage of Amorphous Lactose in Spray Dried Lactose Products," *International Journal of Pharmaceutics* 35:29-36 (1987).

(56) References Cited

OTHER PUBLICATIONS

Welsh, D. T., "The Role of Compatible Solutes in the Adaptation and Survival of *Escherichia coli*," Ph.D. Thesis Submitted to Department of Biological Sciences, University of Dundee. pp. 1-262 . (Aug. 1992).
Whittier, E., "Lactose and its Utilization: A Review," *J. Dairy Sci.* 27(7)505-537 (Jul. 1994).
William and Leopold, "The Glassy State in Corn Embryos" Plant Physiology 89:977-981 (1979).
Williams et al., "The Temperature Dependence of Relaxation Mechanisms in Amorphous Polymers and Other Glass Forming Liquids", *The Journal of the American Chemical Society* 77: 3701-3707 (1955).
Wolff, J. A. et al., "Grafting Fibroblasts Genetically Modified to Produce L-Dopa in a Rat Model of Parkinson Disease," *Proc. Natl. Acad. Sci.* 86:9011-9014 (Nov. 1989).
Xi, Y. G. et al., "Amphotericin B Treatment Dissociates in Vivo Replication of the Scrapie Agent From PrP Acummuiation", *Nature* 356:598-601 (Apr. 1992).
York, "Powdered Raw Materials: Characterizing Batch Uniformity," *Respiratory Drug Delivery IV, Programs and Proceedings*, edited by Byron, Dalby and Farr: 83-91 (1994).
Yoshioka, M. el al., "Crystallisation of Indomethacin From the Amorphous State Below and Above Its Glass Transition Membrane," *Journal of Pharmaceutical Sciences* 83(12):1700-1705 (Dec. 1994).
U.S. Appl. No. 60/060,337, filed Sep. 1997, Kabalnov.
Office Action in U.S. Appl. No. 12/258,163 dated Sep. 28, 2009.
Office Action in U.S. Appl. No. 11/317,839 dated Dec. 23, 2009.
Office Action in U.S. Appl. No. 11/317,839 dated Apr. 13, 2009.
Office Action in U.S. Appl. No. 11/317,839 dated Sep. 25, 2008.
Office Action in U.S. Appl. No. 11/317,523 dated Oct. 1, 2009.
Office Action in U.S. Appl. No. 11/317,523 dated Apr. 10, 2009.
Office Action in U.S. Appl. No. 11/317,523 dated Sep. 25, 2008.
Office Action in U.S. Appl. No. 12/012,827 dated Oct. 21, 2009.
Schröder, et al., "Influence of Bulk and Tapped Density on the Determination of the Thermal Conductivity of Powders and Blends", AAPS Pharm Sci. Tech. 2007, vol. 8 No. 3, Article 78, pp. E1-E8.
Adjei et al., "Pulmonary Delivery of Peptide Drucs: Effect of Particle Size on Bioavailability of Leuprolide Acetate in Healthy Male Volunteers", Jun. 1990, Pharmaceutical Research, 7(6), pp. 565-569).
Block, et al., "Solubility and dissolution of the triamcinolons acetonide", J. Pharm. Sci., 1973, 62(4), p. 617-621.
Bustami, et al., "Generation of Micro-Particles of Proteins for Aerosol Delivery Using High Pressure Modified Carbon Dioxide", Pharm. Res., 2000, pp. 1360-1366, vol. 17, No. 11.
Christensen, et al., "Preparation of Redispersible Dry Emulsions by Spray Drying", Int. J. of Pharm., 2001, pp. 187-194.
Cicogna et al., "Efficacy of prophylactic aerosol amphotericin 13 lipid complex in a rat modal of pulmonary aspergilosis", Antimicrobial Agents and Chemotherapy, 1997, 41 (2), p. 259-261.
Controlled Release Society, Inc.
Haitsma, et al., "Exogenous Surfactant as a Drug Delivery Agent", Adv. Drug Del. Rev., 2001, pp. 197-207.
International Search Report, PCT/US01/24038, issued Jul. 17, 2002.
International Search Report, PCT/US02/13145, dated Aug. 20, 2002 . . . .
JM. Goldman et al., "Inhaled Micronised Gentamicin Powder: A New Delivery System," Thorax, BMJ Publishing Group. GB, vol. 45, No. 12, Dec. 1990, p. 939-940 XP001057935, cited by other.
Johansen, et al., "Technological Considerations Related to the Up-Scaling of Protein Microencapsulation by Spray-Drying", Eur. J. of Pharm. And Biopharm., 2000, pp. 413-417.
Morel, et al., "Crossregulation betwen Th1 and Th2 cells", Critical Reviews in Immunology U.S., 1998, pp. 275-303, vol. 18, No. 4.
Roitt, et al., "Roitt's Essential Immunology 10th Ed.", Blackwell Science, Chapter 20—Autoimmune diseases, 2001, pp. 442 & 449.
Sasaki, et al., "Human immunodeficiency viris type-1 specific immune responses induced by DNA vaccination are greatly enhances by manna-coated DIC14-amidine", Euro. J. of Immunology, Dec. 1997, pp. 3121-3129, vol. 27, No. 12.
Shibata, et al., "Chitin Particle-Induced Cell-Mediated Phagocytosis Initiates IL-12 Production", J. of Immunology, 1997, pp. 2462-2467, vol. 159, No. 5.
Swarbrick et al., Encyclopedia of Pharmaceutical Technology 1994, vol. 9, pp. 288-290.
Office Action in U.S. Appl. No. 09/219,736 (patented as U.S. Pat. No. 6,565,885) dated Jun. 29, 1999.
Office Action in U.S. Appl. No. 09/219,736 (patented as U.S. Pat. No. 6,565,885) dated Dec. 20, 2000.
Office Action in U.S. Appl. No. 09/219,736 (patented as U.S. Pat. No. 6,565,885) dated Aug. 29, 2001.
Office Action in U.S. Appl. No. 09/218,212 (patented as U.S. Pat. No. 6,309,623) dated May 17, 1999.
Office Action in U.S. Appl. No. 09/218,212 (patented as U.S. Pat. No. 6,309,623) dated Jul. 28, 2000.
Office Action in U.S. Appl. No. 09/218,212 (patented as U.S. Pat. No. 6,309,623) dated Dec. 20, 2000.
Office Action in U.S. Appl. No. 09/218,209 (patented as U.S. Pat. No. 6,433,040) dated May 26, 1999.
Office Action in U.S. Appl. No. 09/218,209 (patented as U.S. Pat. No. 6,433,040) dated Feb. 15, 2000.
Office Action in U.S. Appl. No. 09/218,209 (patented as U.S. Pat. No. 6,433,040) dated Jan. 29, 2001.
Office Action in U.S. Appl. No. 09/218,213 (patented as U.S. Pat. No. 6,946,117) dated Jun. 29, 1999.
Office Action in U.S. Appl. No. 09/218,213 (patented as U.S. Pat. No. 6,946,117) dated Apr. 28, 2000.
Office Action in U.S. Appl. No. 09/218,213 (patented as U.S. Pat. No. 6,946,117) dated Nov. 16, 2000.
Office Action in U.S. Appl. No. 09/218,213 (patented as U.S. Pat. No. 6,946,117) dated May 19, 2004.
Office Action in U.S. Appl. No. 09/886,296 dated Jun. 22, 2009.
Office Action in U.S. Appl. No. 09/866,296 dated Dec. 5, 2008.
Office Action in U.S. Appl. No. 09/886,296 dated Apr. 22, 2008.
Office Action in U.S. Appl. No. 09/886,296 dated Nov. 9, 2007.
Office Action in U.S. Appl. No. 09/886,296 dated Mar. 28, 2007.
Office Action in U.S. Appl. No. 09/886,296 dated Jun. 6, 2006.
Office Action in U.S. Appl. No. 09/886,296 dated Nov. 2, 2005.
Office Action in U.S. Appl. No. 09/886,296 dated Apr. 16, 2004.
Office Action in U.S. Appl. No. 09/886,296 dated Jul. 21, 2003.
Office Action in U.S. Appl. No. 09/886,296 dated Dec. 11, 2002.
Office Action in U.S. Appl. No. 09/886,296 dated Jun. 19, 2002.
Office Action in U.S. Appl. No. 10/096,780 (patented as U.S. Pat. No. 7,306,787) dated Jan. 25, 2006.
Office Action in U.S. Appl. No. 10/096,780 (patented as U.S. Pat. No. 7,306,787) dated Apr. 19, 2005.
Office Action in U.S. Appl. No. 10/096,780 (patented as U.S. Pat. No. 7,306,787) dated Jun. 17, 2004.
Office Action in U.S. Appl. No. 10/096,760 (patented as U.S. Pat. No 7,306,787) dated May 20, 2003.
Office Action in U.S. Appl. No. 10/096,780 (patented as U.S. Pat. No. 7,306,787) dated Oct. 2, 2002.
Office Action in U.S. Appl. No. 10/612,393 dated Aug. 1, 2006.
Office Action in U.S. Appl. No. 10/612,393 dated Feb. 9, 2006.
Office Action in U.S. Appl. No. 10/612,393 dated Aug. 10, 2005.
Office Action in U.S. Appl. No. 10/612,393 dated May 4, 2005.
Office Action in U.S. Appl. No. 11/076,430 dated Mar. 3, 2010.
Office Action in U.S. Appl. No. 11/076,430 dated May 11, 2009.
Office Action in U.S. Appl. No. 11/076,430 dated Nov. 13, 2008.
Office Action in U.S. Appl. No. 09/862,764 (patented as U.S. Pat. No. 6,638,495) dated Nov. 1, 2002.
Office Action in U.S. Appl. No. 10/644,265 (patented as U.S. Pat. No. 7,628,978) elated Mar. 20, 2008.
Office Action in U.S. Appl. No. 10/644,265 (patented as U.S. Pat. No. 7,628,978) dated Feb. 1, 2007.
Office Action in U.S. Appl. No. 10/644,265 (patented as U.S. Pat. No. 7,628,978) dated May 9, 2006.
Office Action in U.S. Appl. No. 10/644,265 (patented as U.S. Pat. No. 7,628,978) dated Oct. 7, 2005.
Office Action in U.S. Appl. No. 09/999,071 (patented as U.S. Pat. No. 7,205,343) dated Jan. 18, 2006.
Office Action in U.S. Appl. No. 09/999,071 (patented as U.S. Pat. No. 7,205,343) dated Aug. 12, 2005.

(56) References Cited

OTHER PUBLICATIONS

Office Action in U.S. Appl. No. 09/999,071 (patented as U.S. Pat. No. 7,205,343) dated Oct. 7, 2004.
Office Action in U.S. Appl. No. 09/999,071 (patented as U.S. Pat. No. 7,205,343) dated Jan. 23, 2004.
Office Action in U.S. Appl. No. 09/999,071 (patented as U.S. Pat. No. 7,205,343) dated Jun. 17, 2003.
Office Action in U.S. Appl. No. 11/675,073 (patented as U.S. Pat. No. 7,393,544) dated Sep. 17, 2007.
Office Action in U.S. Appl. No. 09/720,536 (patented as U.S. Pat. No. 6,630,169) dated Jul. 15, 2002.
Office Action in U.S. Appl. No. 09/568,818 dated Dec. 8, 2008.
Office Action in U.S. Appl. No. 09/568,818 dated Feb. 26, 2008.
Office Action in U.S. Appl. No. 09/568,818 dated Jun. 4, 2007.
Office Action in U.S. Appl. No. 09/568,818 dated Oct. 6, 2006.
Office Action in U.S. Appl. No. 09/568,818 dated Jan. 24, 2006.
Office Action in U.S. Appl. No. 09/568,818 dated Apr. 7, 2005.
Office Action in U.S. Appl. No. 09/568,818 dated May 5, 2004.
Office Action in U.S. Appl. No. 09/568,818 dated Jul. 29, 2003.
Office Action in U.S. Appl. No. 09/568,818 dated Nov. 5, 2002.
Office Action in U.S. Appl. No. 09/568,818 dated Apr. 10, 2002.
Office Action in U.S. Appl. No. 09/851,226 (patented as U.S. Pat. No. 7,442,388) dated Dec. 21, 2005.
Office Action in U.S. Appl. No. 09/851,226 (patented as U.S. Pat. No. 7,442,388) dated Mar. 22, 2005.
Office Action in U.S. Appl. No. 09/851,226 (patented as U.S. Pat. No. 7,442,388) dated May 5, 2004.
Office Action in U.S. Appl. No. 09/851,226 (patented as U.S. Pat. No. 7,442,388) dated Jul. 24, 2003.
Office Action in U.S. Appl. No. 09/851,226 (patented as U.S. Pat. No. 7,442,388) dated Feb. 11, 2003.
Office Action in U.S. Appl. No. 09/851,226 (patented as U.S. Pat. No. 7,442,388) dated Jun. 24, 2002.
Office Action in U.S. Appl. No. 10/141,219 dated Mar. 26, 2010.
Office Action in U.S. Appl. No. 10/141,219 dated Aug. 18, 2009.
Office Action in U.S. Appl. No. 10/141,219 dated Jan. 8, 2009.
Office Action in U.S. Appl. No. 10/141,219 dated Jul. 21, 2008.
Office Action in U.S. Appl. No. 10/141,219 dated Nov. 29, 2006.
Office Action in U.S. Appl. No. 10/141,719 dated Mar. 10, 2006.
Office Action in U S. Appl. No. 10/141,219 dated Jun. 6, 2005.
Office Action in U.S. Appl. No. 10/141,719 dated Nov. 15, 2004.
Office Action in U.S. Appl. No. 10/141,219 dated Oct. 23, 2003.
Office Action in U.S. Appl. No. 11/187,757 dated Mar. 26, 2010.
Office Action in U.S. Appl. No. 09/888,311 dated Jan. 8, 2003.
Office Action in U.S. Appl. No. 09/888,311 dated Jun. 25, 2002.
Office Action in U.S. Appl. No. 09/888,311 dated Dec. 5, 2001.
Office Action in U.S. Appl. No. 10/141,032 dated May 20, 2005.
Office Action in U.S. Appl. No. 10/141,032 dated Aug. 17, 2004.
Office Action in U.S. Appl. No. 10/141,032 dated Jul. 16, 2003.
Office Action in U.S. Appl. No. 10/141,032 dated Oct. 23, 2002.
Office Action in U.S. Appl. No. 10/616,448 dated Feb. 25, 2010.
Office Action in U.S. Appl. No. 10/616,448 dated Sep. 25, 2009.
Office Action in U.S. Appl. No. 10/616,448 dated Nov. 14, 2008.
Office Action in U.S. Appl. No. 10/616,448 dated Apr. 16, 2008.
Office Action in U.S. Appl. No. 10/616,448 dated May 4, 2006.
Office Action in U.S. Appl. No. 10/616,448 dated Aug. 19, 2005.
Office Action in U.S. Appl. No. 10/616,448 dated Oct. 25, 2004.
Office Action in U.S. Appl. No. 10/327,510 (patented as U.S. Pat. No. 7,738,102) dated May 4, 2006.
Office Action in U.S. Appl. No. 10/327,510 (patented as U.S. Pat. No. 7,368,102) dated Jun. 28, 2005.
Office Action in U.S. Appl. No. 10/327,510 (patented as U.S. Pat. No. 7,368,102) dated Sep. 20, 2004.
Abbott J et al "Treatment compliance in adults with cystic fibrosis" Thorax 49:115-120 (1994).
Ballmann Manfred et al "Long terra follow-up of changes in FEV1 and treatment intensity during Pseudomonas aeruginosa colonisation in patients with cystic fibrosis" Thorax 53:732-737 (1998).
Brummett RE "Drug-induced Ototoxicity" Drugs 19:412-428 (1980).
Collins Francis S "Cystic Fibrosis: Molecular Biology and Therapeutic Implications" Science 256:774-779 (1992).
Conway SP et al "Compliance with treatment in adult patients with cystic fibrosis" Thorax 51:29-33 (1996).
Corey Mary et al "Longitudinal analysis of pulmonary function decline in patients with cystic fibrosis" J Pediatr 131:809-814 (1997).
Davis Pamela B et al "Cystic Fibrosis" Am J Respir Crit Care Med 154:1229-1256 (1996).
Demko Catherine A et al "Gender Differences in Cystic Fibrosis: Pseudomonas Aeruginosa Infection" J Clin Epidemiol 48(8):1041-1049 (1995).
Eisenberg Jay et al "A Comparison of Peak Sputum Tobramycin Concentration in Patients with Cystic Fibrosis Using Jet and Ultrasonic Nebulizer Systems" Chest 111;955-962 (1997).
Fitzsimmons Stacey C "The changing epidemiology of cystic fibrosis" J Pediatr 122:1-9 (1993).
Fuchs Henry J et al "Effect of Aerosolized Recombinant Human DNase on Exacerbations of Respiratory Symptoms and on Pulmonary Function in Patients with Cystic Fibrosis" N Engl J Med 331:837-642 (1994).
Geller David E et al "Pharmacokinetics and Bioavailability of Aerosolized Tobramycin in Cystic Fibrosis" Chest 122:219-226 (2002).
Henry Richard L et al "Mucoid Pseudomonas aeniginosa is a Marker of Poor Survival in Cystic Fibrosis" Pediatr Pulmonol 12:158-161 (1992).
"Guide for the Evaluation of Hearing Handicap" JAMA 241(19):2055-2059 (1979).
Kerem Eitan et al "Prediction of Mortality in Patients with Cystic Fibrosis" N Engl J Med 326:1187-1191 (1992).
Koch Christian et al "Pathogenesis of cystic fibrosis" Lancet 341:1065-1069 (1993).
Konig Peter et al "Short-Term and Long-Term Effects of Albuterol Aerosol Therapy in Cystic Fibrosis: A Preliminary Report" Pediatr Pulmonol 20:205-214 (1995).
Konstan Michael W et al "Effect of High-Dose Ibuprofen in Patients with Cystic Fibrosis" N Engl J Med 332:848-854 (1995).
Levy Jack et al "Bioactivity of Gentamicin in Purulent Sputum from Patients with Cystic Fibrosis or Bronchiectasis: Comparison with Activity in Serum" J Infect Dis 148(6):1069-1076 (1983).
MacLusky Ian B et al "Long-Term Effects of Inhaled Tobramycin in Patients with Cystic Fibrosis Colonized with Pseudomonas aeruginosa" Pediatr Pulmonol 7:42-46 (1989).
Neu Harold C "Tobramycin: an Overview" J Infect Dis 134:S3-S19 (1976).
Newhouse Michael T "Inhalation of a Dry Powder Tobramycin PulmoSphere Formulation in Healthy Volunteers" Chest 124:360-366 (2003).
Pamukcu A et al "Effects of Pseudomonas aeruginosa Colonization on Lung Function and Anthropometric Variables in Children with Cystic Fibrosis" Pediatr Pulmonol 19:10-15 (1995).
"Physical Tests and Determinations. Aerosols, Metered-Dose Inhalers, and Dry Powder Inhalers" Pharmacopeia US 26th Rev, Natl Formulary. 21st Ed, ch 601 (2003).
Ramsey Bonnie W et al "Response to Letter to the Editor: Aerosolised Tobramycin in Patients with Cystic Fibrosis" N Eng J Med 329:1660 (1993).
Ramsey Bonnie W et al "Intermittent Administration of Inhaled Tobramycin in Patients with Cystic Fibrosis" N Engl J Med 340:23-30 (1999).
Reisman John J et al "Role of conventional physiotherapy in cystic fibrosis" J Pediatr 113:632-636 (1988).
Rosenfeld Margaret et al "Aerosolized Antibiotics for Bacterial Lower Airway Infections: Principles, Efficacy, and Pitfalls" Clin Pulm Med 4(2):101-112 (1997).
Semykim Sergei Yurevich "Effectiveness and Safety in the Use of Ciprofloxacin in Treating the Recurrent Bronchopulmonary Process in Children with Cystic Fibrosis" abstract candidate dissertation, Moscow pp. 8-11, 22-3 (2002).
Touw DJ et al "Inhalation of antibiotics in cystic fibrosis" Eur Respir J 8:1594-1604 (1995).
Winnie Glenna B et al "Respiratory Tract Colonization with Pseudomonas aeniginosa in Cystic Fibrosis: Correlations Between

(56) References Cited

OTHER PUBLICATIONS

Anti-Pseudomonas aeruginosa Antibody Levels and Pulmonary Function" Pediatr Pulmonol 10:92-100 (1991).
Konstan Michael W et al "Infection and Inflammation of the Lung in Cystic Fibrosis" Cystic Fibrosis, Davis ed, Dekker NY pub, Ch 6, pp. 219-276 (1993).
Cystic Fibrosis Foundation Patient Registry Annual Data Report 2004.
International Search Report, PCT/US05/21952 (Sep. 23, 2005).
Supplementary EP Search Report, EP 05766064 (Apr. 1, 2009).
Bibliographic data of EP0472598 (Mar. 4, 1992).
Capsule Connection, Capsule sizing information, obtained online on Oct. 26, 2012 from: http://www.capsuleconnection.com/capsules.
"Albuterol", Merck Index, 12th edition, edited by Susan Budavari, 1996, monograph 217, p. 40-1.
"Amphotericin B", Merck Index, 12th edition, edited by Susan Budavari, 1996, monograph 627, p. 99.
"Estradiol", Merck Index, 12th edition, edited by Susan Budavari, 1996, monograph 3746, p. 630-1.
"Aerosois, Metered-Dose Inhalers, and Dry Powder Inhalers", Pharmacopeial Previews, 22(6): 3065 (1996).
"Pfizer and Inhale Therapeutic Systems Enter Pulmonary Insulin Collaboration for Dry Powder Aerosol Delivery", Health News Daily, vol. 7, No. 13, pp. 4-5 (Jan. 1995).
1, Joachim Seelig, *Handb. Met.—Ligand Interact. Biol. Fluids: Bioinorg. Chem.* § Metal Ion Interactions with Lipids: 698-706 (1995).
Ahtneck et al. "The Molecular Basis of Moisture Effects on the Physical and Chemical Stability of Drugs in the Solid State" Int. J. of Pharmaceutics 62: 87-95 (1990).
Altenbach et al. "Ca2+Binding to Phosphatidycholine Bilayers As Studied by Deuterium Magnetic Resonance. Evidence for the Formation of a Ca2+Complex with Two Phospholipid Molecules" Biochemistry 23: 3913-3920 (1984).
Anchoroquy, Thomas J., Physical Stabilization of DNA Based Therapeutics, 6(9): DDT 463-470 (May 2001).
Babincova et al. "Dextran Enhances Calcium-Induced Aggregation of Phosphatidylserine Liposomes: Possible Implications for Exocytosis" Physiol Res 48(4):319-321 (1999).
Barnett,.A.H., Exhubera Inhaled Insulin: A Review *Int. J. Clin. Pract* 58(4):394-401 (2004).
Belopof'skaya, T.V. et al. "The effect of water as natural plasticizer on thermal properties of denatured DNA studied by calorimetry" Vestrik Sankt-Peterburgskogo Universiteta Journal. Abstract Only. 1999, 2 pages.
Bigsbee, et al. "Solid State Liability of Insulin: Comparison of Crystalline and Amorphous Forms", *Pharmaceutical Research* 10(10): Abstract No. PDD 7418, p. S-279 (1993).
Blakeley, et al., "Dry instant blood typing for beside use", Lancet. 336: 854-855 (1990).
Bögelein, J., et al., "Influence of Amorphous Mannitol on Powder Properties of Spray Dried Trehalose/Dextran Mixtures", [on-line] [retrieved Sep. 2005] Retrieved from the Internet. 2 pages (2003).
Bosquilion, C. et al., "Aerosolization Properties. Surface Composition and Physical State of Spray-Dried Protein Powders", *Journal of Controlled Release*, 99: 357-367 (2004).
Branca, C., et al., "Destructuring effect of rehalose on the tetrahedral network of water: a Raman and neutron diffraction comparison", Physica A 304: 314-318 (2002).
Breitenbach, J., "Melt Extrusion: From Process to Drug Delivery Technology", *European Journal of Pharmaceuticals and Biopharmaceutics* 54: 107-117 (2002).
Buckton et al. "The Use of Gravimetric Studies to Assess the Degree of Crystallinity of Predominantly Crystalline Powders" Int. J. of Pharmaceutics 123: 265-271 (1995).
Buddt et al. "Neutron Diffraction Studies on Phosphatidylcholine Model Membranes" J. Mol. Biol. 134: 673-691 (1979).
Byron, Peter R., et al., Drug Carrier Selection—Important Physicochemcial Characteristics Respiratory Drug Delivery, 5th Ed., Interpharm Press., 103-113., 103-113 (1996).

C. Roth et al., "Production of Hollow Spheres," Paragamon Press, vol. 19 (No. 7), p. 939-942, (Feb. 26, 1988).
Casselyn, M. et al., *Time-Resolved Scattering Investigations of Brom Mosaic Virus Microcrystals Appearance* D58 Acth Cryst. 1568-1570 (2002).
Cevc, G. "Membrane Electrostatics" Biochim Biophys Acta 1031(3): 311-382 (1990)., in particular pp. 330-338.
Chan, Hak-Kim, et al., "Physical Stability of Slamon Calcitonin Spray-Dried Powders for Inhalation", *Journal of Pharmaceutical Sciences*, 93(3): 792-804 (2004).
Chavan, V., et al., "Novel System to Investigate the Effects of Inhaled Volume and Rates of Rise in Simulated Inspiratory Air Flow on Fine Particle Output From a Dry Power Inhaler", *AAPS Pharmisci* 2002; 4(2) article 6, pp. 1-6.
Cline D., "Predicting the Quality of Powders for Inhalation from Surface Energy and Area". *Pharmaceutical Research*, 19(9): 1274-1277 (2002).
Cline, D., et al., "Predicting the Quality of Powders for Inhalation", *Respiratory Drug Delivery VIII* p. 683-685 (2002).
Considine, G.D., et al., *Van Nostrand's Scientific Encyclopedia*, 9th edition, vol. 2, Wiley-Interscience, John Wiley & Sons, Inc., Definition of Vaccines: pp. 3591-3592 (2002).
Dalby, R.N., et al., "Inhalation Therapy: Technological Milestones in Asthma Treatment", *Advanced Drug Delivery*, 55: 779-791 (2003).
D'Cruz, N. "Relationship Between Protein Thermal Stability and Glass Transition in Gelatin Polyol and Gelatin-Water Mixtures", Proceedings of 2004 Meeting IFT, Jul. 12-16, 2004, Las Vegas, NV, Session 17E. Food Chemistry: Proteins, [on-line].
Dellamary et al, "Hollow Porous Particles in Metered Dose Inhalers" Pharm Research (17)2: 168-174 (2000).
Dunbar et al , "Dispersion and Characterization of Pharmaceutical Dry Powder Aerosols," KONA (Feb. 26, 1998).
During, M.J., "Long-Term Behavorial Recovery in Parkinsonian Rats by an HSV Vector Expressing Tyrosine Hydrosylase", *Science*, 266(5189): 856-857 (Nov. 1994).
Duzgunes et al. "Studies on the Mechanism of Membrane Fusion. Role of Head-Group Composition in Calcium- and Magnesium-induced Fusion of Mixed Phospholipid Vesicles" Biochim Biophys Acta 642: 182-195 (1981).
Ebara et al. "Interactions of Calcium Ions with phospholipid Membranes"Langmuir 10: 2267-2271 (Apr. 1994).
Eisenberg et al. "Adsorption of Monovalent Cations to Bilayer Membranes Containing Negative Phospholipids" Biochemistry 18(23):5213-5223 (1979).
Elkordy, et al., Integrity of Crystalline Lysozyme Exceeds that of a Spray-Dried Form. *International Journal of Pharmaceutics*, 247: 79-90 (2002).
Fakes, M., et al., "Moisture Sorption Behavior of Selected Bulking Agents Ued in Lyophillized Products", *PDA J. Pharm. Sci. Technol.* 54(2) 144-149, Abstract only [on-line] [retrieved from Sep. 25, 2005] Retrieved from the Internet (2002).
Fukuoka, et al., "Glassy State of Pharmaceuticals . V. Relaxation During Cooling and Heating of Glass by Differential Scanning Calorimetry", *Chem. Pharm. Bull* 39(8): 2087-2090 (Aug. 1991).
Goldbach et al. "Spray-Drying of Liposomes for a Pulmonary Administration I. Chemical Stability of Phospholipids" Drug Develop Ind Pharm 19(19): 2611-2622 (1993).
Gonda, et al., "Characterization of Hygroscopic Inhalation Aerosols", In: Particle Size Analysis, (Eds. N.G. Stanley-Wood and T. Allen, Wiley Heyden Ltd., NY), pp. 31-43 (1981).
Gordon et al. "Ideal Copolymers and the Second-Order Transitions of Synthetic Rubbers. I. Non-Crystalline Copolymers" J. Appl. Chem. 2: 493-500 (Sep. 1952).
Gupta, A., et al., "Single Virus Particle Mass Detection Using Microresonators with Nanoscale Thickness", *Applied Physics Letters*, 84(11): 1976-1978 (2004).
Hancock et al. "Characteristics and Significance of the Amorphous State in Pharmaceutical Systems" J. of Pharmaceutical Sciences 86(1): 1-12 (Jan. 1997).
Hancock et al. "The Relationships Between the Glass Transition Temperature and the Water Content of Amorphous Pharaceutical Solids" Pharm Research 11(4):471-477 (1994).

(56) References Cited

OTHER PUBLICATIONS

Hancock et al., "A Pragmatic Test of Simple Calorimetric Method for Determing the Fragility of some Amorphous Pharmaceutical Materials", *Pharm. Res.*, 15(5): 762-767 (1998).

Hanes, Justin, "Polymer Microspheres for Vaccine Delivery", Thesis (Ph.D.), dated Sep. 1996, archived by MIT library Jul. 31, 1997 and catalogued on Dec. 5, 1997.

Hauser et al. "Comparative Structural Aspects of Cation Binding to Phosphatidyiserine Bilayers" Biochim Biophys Acta 813: 343-346 (1985).

Hauser et al. "Interactions of Divalent Cations with Phosphatidylserine Bilayer Membranes" Biochemistry 23: 34-41 (1984).

Hrkach et al., "Poly-lactic-co-amino acid) graft copolymers: A class of . . . polymers for bioapplication," Hydrogels and Biodegradable Polymers for Bioapplication (1996), ACS Symposium Series No. 627, pp. 93-101.

Hrkach et al., "Synthase of polylactic acid-co-lysine graft copolymers," Macromolecules 1995, 28(13):4736-4739.

Huster et al. "Investigation of Phospholipid Area Compression Induced by Calcium-Mediated Dextran Sulfate Interaction" Biophys J. 77(2): 879-867 (Aug. 1999).

Huster et al. "Strength of Ca(2+), Binding to Retinal Lipid Membranes: Consequences for Lipid Organization" Biophys J. 78(6): 3011-3918 (Jun. 2000).

Ibrahim; A. L. et al., "Sprah Vaccination With an Improved F Newcastle Disease Vaccine. A Comparison of Efficacy With the B1 and La Sota Vaccines," Br. Vet. J. 139:213-219 (1983).

Iglesias et al., "Adsorption Isotherm of Amorphous Trehalos", *J. Sci. food Agric.* 75:183-186 (1997).

Jacobson et al. "Phase Transition and Phase Separations in Phospholipid Membranes Induced by Changes in Temperature, pH. and Concentration of Bivalent Cations" 14(1): 152-161 (1975).

Jameel, F. et al., "Freeze Drying Properties of Some Oligonucleotides", *Pharmaceutical Development and Technology* 6(2):151-157 (2001).

Kwon et al. "Calcium Ion Absorption on Phosphollpid Bilayers—Theorectical Interpretation" J Jap Oll Chem Soc 43(1): 23-30 (1994).

Lee, G., "Spray Drying of Proteins," Chapter 6, *Rational Design of Stable Protein Formulations, Theory and Practice*, J. F. Carpenter & M. Manning, pp. 135-158 (2002).

Li, Z., et al., "Realistic In Vitro Assessment of Dry Powder Inhalers", *Respiratory Drug Delivery VIII*, pp. 687-689 (2002).

Lin, S.-Y. et al., "Solid Particles of Drug-β-Cyclodextrin Inclusion Complexes Directly Prepared by a Spray-Drying Technique", International Journal of Pharmaceutics, 56:249-259 (1989).

Lis et al. "Adsorption of Divalent Cations to a Variety of Phosphatidylcholine Bilayers" Biochemistry 20: 1771-1777 (1981).

Lis et al. "Binding of Divalent Cations to Dipatmitoylphosphtiatidyicholine Bilayers and its Effect on Bilayer Interaction" Biochemistry 20: 1761-1770 (1981).

Liu, Jinsong et al., "Dynamics of Pharmaceutical Amorphous Solids: The Study of Enthalpy Relaxation by Isothermal Microcalorimetry", *Journal of Pharmaceutical Sciences* 91(8):1853-1862 (2002).

Louey, M. D. et al., "Controlled Release Products for Respiratory Delivery", APR, 7(4):82-87 [on-line] retrieved 09/20051 <http://www.americanpharmceuticalreview.com.article.aspx?article=77 (2004).

Masters, K Spray Drying Handbook, 5th ed., Chapters 13 and 15, pp. 491-537 and 587-642 (1991).

Masters, K. Spray Drying Handbook, England; Longman Scientific & Technical and John Wiley & Sons, Inc., 5th ed. Chapter 8, pp. 309-352 (1991).

Masters, K. Spray Drying Handbook, England; Longman Scientific & Technical, 5th ed., pp. 640-842 (1991).

Millqvist-Fureby et al. "Spray-Drying of Trypsin—Surface Characterisation and Activity Preservation" Int. J. Pharm. 188: 243-253 (1999).

Millqvist-Fureby et al. "Surface Characterisation of Freeze-Dried Protein/Carbohydrate Mixtures" Int. J. Pharm. 191: 103-114 (1999).

Molina, M. C. et at., "The Stability of Lyophilized Lipid/DNA Complexes During Prolonged Storage," J. Pharm. Sci. 93(9):2259-2273, abstract only: one page, [on-line] [retrieved Sep. 2005] Retrieved from the Internet , (2004).

Mumenthaler, M. et al., "Feasibility Study on Spray-Drying Protein Pharmaceuticals: Recombinant Human Growth Hormone and Tissue-Type Plasminogen Activator," *Clinical Research* 11(1): 12-20 (1994).

Murphy, Brian R. et al., *Fields Virology*, vol. 1, Chapter 16, *Immunization Against Virus Disease*, 467, at p. 468, first full paragraph, first column, lines 26-33 (Bernard N. Fields et al. eds., Lippincott-Raven Publishers, 3rd ed. 1996).

Mutterlein, et al., "New Technology for Generating Aerosols—Preliminary Results with the Piezoelectrical Pocket-Inhaler", *J. Aerosol Med.*, 1:231 (1988).

Natarajan, P., Crystallization Conditions for VIPER Entries [on-line] [retrieved Nov. 4, 2004] Retrieved from the Internet 5 pages (last updated Jan. 3, 2002).

Nektar Notice of Opposition against EP 939622 B1 (Dec. 5, 2003).

Nektar U.S. Appl. No. 08/044,358, "Compositions and Methods For Nucleic Acid Delivery To The Lunch" filed by Patton et al. Apr. 7, 1993, assigned to Inhale Therapeutic Systems.

Nektar U.S. Appl. No. 08/422,563, filed Apr. 14, 1995, Paper No. 17, Office communication mailed Apr. 3, 1998 (U.S. Pat. No. 5,994,314).

Niven, R. W., "Delivery of Biotherapeutics by Inhalation Aerosol," *Critical Reviews in Therapeutic Drug Carrier Systems*, 12(2&3):151-231 (1995).

Odegard, P. S. et al., "Inhaled Insulin: Exubera", *The Annals of Pharmacotherapy* 39:843-853 (2005).

Ohtake, S. et al., "Effect of pH, Counter Ion and Phosphate Concentration on the Glass Transition Temperature of Freeze-Dried Sugar-Phosphate Mixtures", *Pharmaceutica Research* 21(9):1615-1621(2004).

Okamoto, H. et al., "Dry Powders for Pulmonary Delivery of Peptides and Proteins", *Kona* 20:71-83 (2002).

Opposition Papers of European Patent No. EP 1019021 (European Application No. 98950826.2) Dated: Jun. 3, 2004 through Nov. 15, 2006.

Owens, D. F., et al., "Alternative Routes of Insulin Delivery," *Diabetic Medicine* 20:886-898 (2003).

Parassassi et al. "Calcium-Induced Phase Separation in Phospholipid Bilayers. A Fluorescence Arisotropy" Cellular and Molecul Bio 32(3): 261-266 (1986).

Patel, M. M. et al., "Degradation Kinetics of High Molecular Weight Poly(L. Lactide) Microspheres and Release Mechanism of Lipid: DNA Complexes", *Journal of Pharmaceutical Sciences*, 93(10): 2573-2584 (2004).

Pearlman et al., "Formulation Strategies for Recombinant Proteins: Human Growth Hormone and Tissue Plasminogen Activator", *Therapeutic Peptides and Proteins, Formulation, Delivery and Targeting*, Cold Spring Harbour, New York, pp. 23-30 (1989).

Persson, G. and J.E. Wiren. The bronchodilator response from inhaled terbutaline is influenced by the mass of small particles: a study on dry powder inhaler (Turbuhaler) Eur. Respir. J. 2:253-256 (1989).

Phillips, E. et al., "Size Reduction and Proteins by Jet-Milling", *Respiratory Drug Delivery VI.* pp. 161-167 (1998).

Pikal, M. J. et al., Errata of "The Stability of Insulin in Crystalline and Amorphous Solids: Observation of Greater Stability for the Amorphous Form," *Pharmaceutical Research* 15(2):362-363 (1998).

Product Sheet for Intal® Inhaler.

Reboiras, M.D. "Activity Coefficients of $CaCl_2$ and $MgCl_2$ in the Presence of Dipalmitoylphosphatidycholine-Phosphatidylinositol Vesicles in Aqueous Media" Bioelectrochemistry and Bioenergentics 39: 101-108 (1996).

Ringe, D. et al., "The Glass Transition In Protein Dynamics: What it is, Why it Occurs, and How to Exploit It", *Biophys. Chem.* 105(2-3):667-680, Abstract only. [on-line] [retrieved Nov. 19, 2004] Retrieved from the Internet (2003).

Rosen, Surfactants and Interfacial Phenomena, Second Edition, John Wiley & Sons, New York, pp. 326-329 (1989).

(56) References Cited

OTHER PUBLICATIONS

Royali et al. "Characterisation of Moisture Uptake Effects on the Glass Transitional Behaviour of an Amorphous Drug Using Modulated Temperature DSC" Int. J. Pharm. 192: 39-46 (1999).
Satoh, Koichi, "Determination of Binding Constants of Ca2+, Na+, and Cl- Ions to Liposomal Membranes of Dipelmitaoylphosphatidylcholine at Gel Phase by Particle Electrophoresis", Biochem. Biophys. Acta 1239:239-248 (1995).
Schram, L., "The Language of Colloid and Interface Science, A Dictionary of Terms", American Chem. Soc. p. 157 (1993).
Sciarra et al., "Aerosols", *Remington's Pharmaceutical Sciences*, Chap. 93, 17 Ed., Mack Publishing Company, Altonso R. Gennaro, editor, pp. 1662-1677 (1985).
Seddon, J.M. "Structure of the Inverted Hexagonal (HII) Phase, and Non-Lamellar Phase Transitions of Lipids" Biochim Biophys Acta 1031:1-69 (1990). , in particular p. 43-44 and 49-50.
Shah et al. "The Ionic Structure of Sphingomyelin Monolayers" Biochem Biophys Acta 135: 184-187 (1967).
Sharma, V.K. et al., "Effect of Vacuum Drying on Protein-Mannitol Interactions: The Physical State of Mannitol and Protein Structure in the Dried State", AAPS PharmSciTech 5(1) Article 10:1-12 [on-line] [retrieved] Retrieved from the Internet (2004).
Shavnin et al. "Cholesterol Affects Divalent Cation-Induced Fusion and Isothermal Phase Transitions of Phospholipid Membranes" Biochim Biophys Acta 946: 405-416 (1988).
Slade and Levine, "The Glassy State Phenomenon in Food Molecules." *The Glassy State in Foods*, Blanshard & Lillford, editors: 35-101 (1993).
Sonner, C. et al., "Spray-Freeze-Drying for Protein Powder Preparation: Particle Characterization and a Case Study With Trypsinogen Stability", *Journal of Pharmaceutical Sciences* 91(10):2122-2139 (2002).
SPI Polyols™ "What are Polyols? What do Polyols do? What are Polyols' functionality?", [on-line] [retrieved Jun. 25, 2004] Retrieved from the Internet one page (2003).
Sugisaki et al. "Calorimetric Study of the Glassy State. IV. Heat Capacities of Glassy Water and Cubic Ice" Bulletin of the Chemical Society of Japan 41: 2591-2599 (Nov. 1968).
Sussich, F. et al., "Reversible Dehydration of Trehalose and Anhydrobiosis: From Solution State to an Exotic Crystal?", *Carbohydrate Research* 334: 165-176 (2001).
Tatuiian, S.A. "Binding of Alkaline-Earth Metal Cations and Some Anions to Phosphatidylcholine Liposomes" Eur. J. Biochem. 170: 413-420 (1987).
Tatulian, S.A. "Evalutation of Divalent Cation Binding to Phosphatidylserine Membranes by an Analysis of Concentration Dependence of Surface Potential" J. Colloid Interface Science 175: 131-137 (1995).
Thatcher, E., "Quantitation of Virus" [on-line] retrieved I 1/0 1/041 Retrieved rom the internet 4 pages, (last updated Jan. 5, 2002).
To et al., "Collaspe. a Structural Transition in Freeze Dried Carbohydrates", *J. Fd. Technol.* 13: 567-581 (1978).
Ulrich, "Biophysical Aspects of Using Liposomes as Delivery Vehicles", *Bioscience Reports* 22(2): 129-150 (2002).
Verstraeten et al. "Effects of Al(3+) and Related Metals on Membrane Phase State and Hydration: Correlation with Lipid Oxidation" Arch Biochem Biophys 375(2): 340-346 (Mar. 15, 2000).
Wang, et al., eds. *Stability and characterization of protein and peptide drugs*, Table of Contents, 6 pages (1993).
Weers, "Colliodal Particles in Drug Delivery," Current Opinion in Colloid & Interface Science (1998), 3:540-544.
Whipps et al. "Growth of Calcium Monohydrate at Phospholipid Langmuir Monolayers" J Cryst Growth 192: 243-249 (1998).
Yamaguchi et al. "Adsorption of Divalent Cations onto the Membrane Surface of Lipid Emulsion" Colloids and Surfaces B: Biointerfaces 5: 49-55 (1995).
Yoshida, H. et al., "Absorption of Insulin Delivery to Rabbit Trachea Using Aerosol Dosage Form," Journal of Pharmaceutical Sciences 68(5): 670 (May 1979).

Yoshinari, T. et al., "Moisture Induced Polymorphic Transition of Mannitol and its Morphological Transformation", *International Journal of Pharmaceutics*, 247:69-77 (2002).
Zarif et al., "Amphotericin B. Cochleates as a Novel Oral Delivery System," International Symposium, p. 965-965 (1999).
Zubay, G. Biochemistry, Second Edition, pp. 211-256 "Nucleotides and Nucleic Acids" (1988).
Zubay, G. Biochemistry, Second Edition. pp. 39 & 169, Table 5-6 Major Steroid Hormones (1988).
Advertisement for "Stop 'n Grow" manufactured by The Mentholatum Co. Ltd., East Kilbride, Scotland G74 5P3.
Agrimi, U., et al. "Amyloid, Amyloid-Inducers, Cytokines and Heavy Metals in Scrapie and Other Human and Animal Subacute Spongiform Encephalopathies: Some Hypothesis", *Med. Hypotheses*. 40(2): 113-116 (1993).
Akers, M.J., et al., "Glycine Crystallization During Freezing: The Effects of Salt Form, pH, and Ionic Strength", *Pharmaceutical Research* 12(10):1457-1461 (1995).
Akoh, et al., "One-stage synthesis of raffinose fatty acid polyesters", *J. Food Sci.*, 52:1570-1576 (1987).
Alberts, B., et al., *Molecular Biology of the Cell*, $2^{nd}$ ed., Garland Publishing Inc., Ch. 2, p. 58 (1989).
Aldous, et al., "The Crystallization of Hydrates from Amorphous Carbohydrates", *Cryo-Letters*, 16:181-186 (1995).
Allen, D.J., et al. "Determination of the Degree of Crystallinity of Solid-Solid Equilibria", *J. Pharm. Sci.*, 58:1190-1193 (1969).
Allison, S.D., et al., "Mechanisms of Protection of Cationic Lipid-DNA Complexes During Lyophilization", *Journal of Pharmaceutical Sciences* 89(5): 682-691 (2000).
Allison, S.D. and Anchordoquy, Thomas J., *Lyophilization of Nonviral Gene Delivery Systems*, Methods in Molecular Medicine, Nonviral Vectors for Gene Therapy, Ch. 18, p. 225-252 (Mark A. Findeis ed., Human Press, 2001).
Amidon, G.E., et al., "Powder Flow Testing in Preformulation and Development", *Pharm. Manuf.*, 2: 20-31 (1985).
Anekwe, J., et al., "Relaxation Constants as a Predictor of Protein Stabilization", *Biocalorimetry: Applications of Calorimetry in the Biological Science*, J.E. Ladbury and B.Z. Chowdhry, editors, John Wiley & Sons, pp. 243-251 (1998).
Bandara, G., et al., "Interarticular Expression of Biologically Active interleukin 1- Receptor-Antagonist Protein by Ex Vivo Gene Transfer", *Proc. Natl. Acad. Sci.*, 90:10764-10768 (Nov. 1993).
Bell, J.H., et al., "Dry Powder Aerosols I: A New Powder Inhalation Device", *J. Pharm, Sci.*, 60(10): 1559-1564 (Oct. 1971).
Ben-Jenria, Abdellaziz, et al., "Large Powous Particles for Sustained Protection from Carbochol-Induced Bronchoconstriction in Guinea Pigs", *Pharma. Res.*, vol. 16, No. 4, p. 555-561.
Blakeley, et al., "Dry instant blood typing for bedside use", *Lancet*, 336: 854-855 (1990).
Bootsma, H.P.R., et al., "β-Cyclodestrin as an Excipient in Solid Oral Dosage Forms: In Vitro and In Vivo Evaluation of Spray-Dried Diazepan-β-Cyclodestrin Products", *International Journal of Pharmaceutics* 51:213-223 (1989).
Borgstrom, et al., "Lung Deposition of Budesonide Inhaled via Turbuhaler", *Eur. Respir. J.*, p. 69-73 (Feb. 26, 1994).
Branchu, S., et al., "The Effect of Cyclodestrins on Monomeric. Protein Unfolding", *Biocalorimetry: Applications of Calorimetry in the Biological Sciences*, J.E. Ladbury and B.Z. Chowdhry (eds.), John Wiley & Sons, Ltd., 297-301 (1998).
Branchu, S., et al., "Hydroxypropyl-β-Cyclodextrin Inhibits Spray-Drying-Induced Inactivation of β-Galactosidase", *Journal of Pharmaceutical Sciences* 88(9): 905-911 (1999).
Brange, et al., "Chemical Stability of Insulin. I. Hydrolytic Degradation During Storage of Pharmaceutical Preparations", *Pharmaceutical Research* 9(6): 715-726 (1992).
Broadhead, J., et al., "The Effect of Process and Formulation Variable on the Properties of Spray-Drive β-Galactosidase", *J. Pharm. Pharmacol.* 46(6): 458-567 (Jun. 1994).
Broadhead, J. et al., *The Spray Drying of Pharmaceuticals*, 18 Drug Development and Industrial Pharmacy, p. 1169-1206 (1992).
Brown, "A Therapeutic Panorama of the Spongiform Encephalopathies", *Antiviral Chem. Chemother.* 1(2): 75-83 (1990).

(56) References Cited

OTHER PUBLICATIONS

Buitink. Julia, at al, *High Critical Temperature above Tg May Contribute to the Stability of Biological Systems*, 79 Biophysical Journal, 1119-1128 (Aug. 2000).
Burvall, et al., "Storage of Lactose-Hydrolised Dried Milk: Effect of Water Activity on the Protein Nutritional Value", *Journal of Dairy Research* 45: 381-389 (1978).
Byström, et al., "Microcalorimetry—A Novel Technique for Characterization of Powders", *Respiratory Drug Delivery IV*, p. 297-302 (1994).
Carpenter, John F., et al., "Rational Design of Stable Lyophilized Protein Formulations: Some Practical Advice", *Pharmaceutical Res.*, 14(8): 969-975 (1997).
Caughey, et al., "Sulphated Polyanion inhibition of Scrapie-Associated PrP Accumulation in Cultured Cells", *J. Virol.*, 67(2): 643-650 (1993).
Chan, et al., "Formulation of Vaccine Ajuvant Muramyldipeptides (MDP) 1. Characterization of Amorphous and Crystalline Forms of a Muramyldipeptide Analogue", *Pharmaceutical Research*, 5(8): 523-527 (1988).
Chan, Hak-Kim, et al., "Solid State Characterization of Spray-Dried Powders of Recombinant Human Deoxyribonuclease (RhDNase)", *Journal of Pharmaceutical Sciences*, 87(5): 647-654 (1998).
Chavan, V., et al., "Effect of Rise in Simulated Inspiratory Flow Rate and Carrier Particle Size on Poweder Emptying From Dry Powder Inhalers", *AAPS Pharmsci* 2000; 2(2) article 10 [on-line] Retrieved from the Internet <URL: http://www.pharmsci.org> 7 pages (2000).
Chavan, V., et al., Effect of Particle Size and Rise in Simulated Inspiratory Flow Rate on Device Emptying in a Dry Powder Inhaler SYstem, [on-line] [retrieved Jan. 7, 2005] Retrieved from the Internet <URL: http://www.aapspharmsci.org/abstracts/AM_1999/1001.htm> 1 page (1999).
Chawla, et al., "Production of Spray Dried Salbutamol Sulphate for Use in Dry Powder Aerosol Formulation", *International Journal of Pharmaceutics*, 108: 233-240 (1994).
Chiou, et al., "Pharmaceutical Applications of Solid Dispersion Systems", *J. Pharm.*, 60(9): 1281-1302 (1971).
Cleland, et al., "The Development of Stable Protein Formulations: A Close Look at Protein Aggregation, Deamidation and Oxidation", *Critical Reviews in Therapeutic Drug Carrier Systems*, 10(4): 307-377 (1993).
Colaco, et al., "Extraordinary Stability of Enzymes Dreid in Trehalose: Simplified Molecular Biology", *Bio/Technology* 10: 1007-1011 (1992).
Colaco, et al, "Trehalose Stabilization of Biological Molecules", *Biotechnol. Internet.*, pp. 345, 347-350 (1992).
Colaco, et al., "Chapter 14: Chemistry of Protein Stabilization by Trehalose", *ACS Symposium Series 567, Formulation and Delivery of Proteins and Peptides*, J.L. Cleland & R. Langer, pp. 222-240 (1994).
Constantino, et al., "Moisture-Induced Aggregation of Lyophilized Insulin", *Pharmaceutical Research*, 11(1): 21-29 (1994).
Constantino, H.R., at al., "Effect of Mannitol Crystallization on the Stability and Aerosol Performance of a Spray-Dried Pharmaceutical Protein. Recombinant Humanized Anti-IgE Monoclonal Antibody", *Journal of Pharmaceutical Sciences*, 87(11): 1406-1411 (1998).
Craig, I.D., et al, "Maillard Reaction Kinetics in Model Preservation Systems in the Vicinity of the Glass Transition: Experiment and Theory", *J. Agric. Food Chem.* 49(10: 4706-4712 (2001).
Crommelin, et al., "Liposomes", Chapter 3, *Colloidal Drug Delivery Systems*, J. Kreuter, editor: 73-190 (1994).
Crowe, et al., "Are Freezing and Dehydration Similar Stress Vectors? A Comparison of Modes of Interaction of Stabilizing Solutes with Biomolecules", *Cryobiol.* 27: 219-231 (1990).
Crowe, et al., "Interactions of Sugars with Membranes", *Biochimca et Biophysica Acta*, 947: 367-384 (1988).
Crowe, John H., et al., "The Role of Vitrification in Anhydrobiosis", *Annu. Rev. Physiol.*, 60: 73-103 (1998).
Crowe, Lois M., et al., "Is Trehalose Special for Preserving Dry Biomaterials?", *Biophysical Journal*, 71: 2087-2093 (1996).
D'Hondt, "Possible Approaches to Develop Vaccines Against Hepatitis A", *Vaccine* 10 (Supplement 1): 548-852 (1992).
Daemen, et al., "The Destruction of Enzymes and Bacteria During the Spray-Drying of Milk and Whey, 2. The Effect of the Drying Conditions", *Neth. Milk Dairy J.*, 36: 211-229 (1982).
Dalby, R.N., et al., "Droplets Drying and Electrostatic Collection a Novel Alternative to Conventional Communication Techniques", *Journal of Biopharmceutical Sciences* 3(1/2): 091-099 (1992).
Dalby, et al., "Relationship Between Particles Morphology and Drug Release Properties After Hydration of Aerosols Properties Containing Liposome Forming Ingredients", *Pharmaceutical Research*, 5(10): 8-94, Abstract PD 888 (1988).
Darrington, et al., "Evidence for a Common Intermediate in Insulin Deamidation and Covalent Dimer Formation: Effects of pH and Aniline Trapping in Dilute Acidic elutions", *Journal of Pharmaceutical Sciences*, 84(3): 275-282 (1995).
DeCario, S., et al., "Unexpected Property of Trehakose as Observed by Gyro-Electron Microscopy", *Journal of Microscopy*, 196(1): 40-45 (1995).
DeYoung, "The AeroDose Multidose Inhaler Device Design and Delivery Characteristics", *Respiratory Drug Delivery VI*, p. 91 (1998).
Dose et al., "Survival in Extreme Dryness and DNA-Single-Strand Break ", *Advances in Space Research*, 12(4)221-229 (1992).

* cited by examiner

FIG. 2

Tobramycin Sulfate PulmoSphere
Aerosol Characteristics in Turbospin at 60 LPM

FIG. 3

Tobramycin Sulfate PulmoSphere™
Aerosol Characteristics in Turbospin at 60 LPM

PULMONARY DELIVERY OF AMINOGLYCOSIDE

FIELD OF THE INVENTION

The present invention is directed to the administration of aminoglycosides. In particular, the present invention is directed to compositions and methods for the pulmonary administration of aminoglycosides. According to a preferred embodiment, dry powder aminoglycoside compositions and methods for their administration are provided for the localized treatment of respiratory infections.

BACKGROUND OF THE INVENTION

Aminoglycosides are potent bactericidal agents. Their main mechanism of action is on the bacterial ribosome, which in turn inhibits protein synthesis. They are active against a wide range of gram-positive and gram-negative species as well as mycobacteria. For some serious gram-negative infections, aminoglycosides or aminoglycosides in combination with other antimicrobials may be the drug of choice for *Pseudonomas* and other infections.

Lower respiratory tract infections with *pseudomonas aeruginosa* (Psa) are a major cause of morbidity and mortality among patients with cystic fibrosis (CF) and non-CF bronchiectasis. Once an infection is established, even aggressive antibiotic treatments may only temporarily reduce the number of Psa organisms in the respiratory tract. As a result, many CF patients have persistent Psa infections requiring frequent hospital admissions for intravenous chemotherapy.

Bronchiectasis is a condition characterized by progressive destruction and dilatation of airway walls due to infected retained secretions that result from a failure of airway defenses to maintain the sterile environment of the lower respiratory tract airways and lung parenchyma. The large volumes of infected secretions requiring aggressive antibiotic treatment at the onset of the infection and the presence of marked bacterial resistance to common and often used antibiotics represent significant barriers to effective therapy. The most effective treatment of bronchiectasis remains antibiotic therapy, usually administered systemically orally or by intravenous injection.

Aminoglycosides are considered one of the most useful classes of antibiotics for treating Psa infections. However, antibiotic therapy of a variety of respiratory infections, in particular bronchiectasis, continues to represent a major medical challenge.

One of the major disadvantages of aminoglycosides is that they can induce fairly severe side effects. Aminoglycosides are generally poorly absorbed orally and, for this reason, are given intravenously or intramuscularly. Aminoglycosides active against Psa penetrate into sputum poorly, making it necessary to administer large systemic doses intravenously in order to optimize sputum penetration at the site of infection in the lung. Such high doses can produce both nephrotic and ototoxic effects, often causing permanent renal insufficiency and auditory nerve damage, with deafness, dizziness, and unsteadiness.

At the same time, underdosing and incomplete courses of antibiotics are part of the problem of ineffective therapy. Potential consequences of underdosing respiratory tract infections include inadequate pathogen eradication, development of antibiotic resistance and lengthened eradication times, as well as potential for persistent clinical symptoms due to increasing lung injury, bronchiectasis, scarring, and premature death.

The overuse of antibiotics in the treatment of respiratory infections is a major problem and is increasingly regarded as such by both the medical community and the pharmaceutical industry. The Center for Disease Control (CDC) considers the growing problem of antibiotic resistance to be one of the most important public health challenges of our time. The CDC views overprescription of antibiotics as one of the prime culprits for the growing antibiotic resistance problem.

In view of the above problems in antibiotic therapies, research has primarily focused on the discovery of new molecules to provide possible solutions. Alternatively, the potential effectiveness of treating infections of the respiratory tract with aminoglycosides administered by new drug delivery technologies such as inhalation aerosols has been investigated. In particular, aerosolized antibiotics have been administered by small volume nebulizers (SVN) driven ultrasonically or by air compressors.

For two decades, inhaled antibiotics have been used effectively for ameliorating chronic pulmonary infections in conditions such as cystic fibrosis and non-CF bronchiectasis. To date, the U.S. Food and Drug Administration (FDA) has approved only one aerosolized antiinfective: TOBI® (Chiron Corporation, Seattle, Wash.). TOBI is a tobramycin solution for inhalation by nebulization. Tobramycin (O-3-amino-3-deoxy-α-D-glucopyranosyl-(1-4)-O-[2,6-diamino-2,3,6-trideoxy-α-D-ribo-hexopyranosyl-(1-6)]-2-deoxy-L-streptamine) is a water soluble, aminoglycoside antibiotic having a molceular weight of 467.52 g/mol. Tobramycin is effective against gram negative pathogens, in particular *Pseudomonas aeruginosa*, the key infective agent in CF patients.

The formulated TOBI product is an aqueous solution, which is sterile, clear, slightly yellow, non-pyrogenic, and is pH and salinity adjusted. It comprises 300 mg of tobramycin free base in 5 ml of sodium chloride (2.25 mg/ml) at pH 6.0 and is stable at 2-8 C for two years, or 28 days at room temp. The solution darkens in intense light. At pH 6.0, approximately 2.2 of the 5 tobramycin amino groups have been converted to sulfate salts. A dose is a single 300 mg ampoule bid (12 hours apart).

Patients receive a 28 day "on" therapy followed by a 28 day "off" period, to reduce the potential for development of resistant bacterial strains. Of the 300 mg inhaled, only approximately 10% or 30 mg is delivered to the lung. Systemic tobramycin given by IV injection has serious adverse effects including renal and ototoxicity. High IV doses are typically given due to poor penetration of the drug across the lung endothelium and into sputum. Clinical studies with TOBI have shown that inhaled tobramycin may lead to tinitus and voice alteration.

Nebulization has many well documented disadvantages, including extended administration time, high cost, poor efficiency and reproducibility, risk of bacterial contamination, and the need for bulky compressors or gas cylinders. These disadvantages likely have an impact on patient compliance.

Pulmonary delivery by aerosol inhalation has received much attention as an attractive alternative to intravenous, intramuscular, and subcutaneous injection, since this approach eliminates the necessity for injection syringes and needles. Pulmonary delivery also limits irritation to the skin and body mucosa which are common side effects of transdermally, iontophoretically, and intranasally delivered drugs, eliminates the need for nasal and skin penetration enhancers (typical components of intranasal and transdermal systems that often cause skin irritation/dermatitis), is economically attractive, is amenable to patient self-administration, and is often preferred by patients over other alternative modes of administration. Administration of aminoglycoside dry powder aerosols to the lung has been attempted, but inefficient delivery devices and/or poorly dispersible lactose formulations limited these studies.

Dry powder inhalers are known in the art as disclosed, for example, in U.S. Pat. Nos. 5,458,135; 5,740,794; 5,775,320; and 5,785,049, and in copending U.S. application Ser. Nos. 09/004,558 filed Jan. 8, 1998, Ser. No. 09/312,434 filed Jun. 4, 1999, 60/136,518 filed May 28, 1999, and 60/141,793 filed Jun. 30, 1999, all of which are hereby incorporated in their entirety by reference.

In addition, U.S. Pat. No. 5,875,776 discloses a dry powder inhaler and discloses antibiotics such as gentamicin sulfate, amikacin sulfate, and tobramycin sulfate, among an extensive list of agents suitable for administration by the devices disclosed therein. No examples of formulations are disclosed. WO 00/35461 further discloses a method for treating bronchiectasis comprising the administration of an aminoglycoside aerosol.

A hollow porous tobramycin dry powder formulation was engineered and delivered from the Turbospin (PH&T, Italy) dry powder inhaler in a recent clinical study. Of the 25 mg of powder loaded into the capsule in the clinical study, only 4.6 mg (18.4%) of active drug substance was delivered to the lung. At this drug loading and efficiency, approximately 6 capsules (ca. 27.6 mg) are required to deliver a lung dose equivalent to the nebulized TOBI product. The requirement for administering at least 6 capsules raises issues with respect to patient compliance for such a therapy.

Despite the advances in discovering newer, broad spectrum antibiotics and drug delivery technologies, there remains a need for improved methods for administering antibiotics such as aminoglycosides. In particular, the maximum safe systemic dosages of aminoglycosides administered according to current therapies provide much less than the dose sufficient to achieve amounts of drug in lung tissue and secretions to exceed the minimum inhibitory capacity (i.e. concentrations capable of eliminating or significantly decreasing the bacterial burden causing the infection in the airways and lung tissues). Thus, therapy is likely to be inadequate while encouraging the emergence of resistant organisms and the development of adverse side effects. There remains a need for a patient-friendly means of administering aminoglycosides to patients which will provide higher localized concentrations of drug in the airway secretions and adjacent lung tissue without the risk of significant systemic side effects. Ideally, such administration must be from a device which is practical such that patient compliance is encouraged. The present invention meets these and other needs.

DEFINITION OF TERMS

As used herein, the term "aminoglycoside" refers to both synthetic and natural antibiotics isolated from species of *Streptomyces* and *Micromonospora* as known in the art and includes, but is not limited to, gentamicin, netilmicin, tobramycin, kanamycin, neomycin, paramecin, amikacin, azithromycin and streptomycin, including pharmaceutically acceptable salts and esters thereof.

As used herein, the term "dry powder" refers to a composition that contains finely dispersed solid particles that are capable of (i) being readily dispersed in or by means of an inhalation device and (ii) inhaled by a subject so that a portion of the particles reach the lungs. Such a powder is considered to be "respirable" or suitable for pulmonary delivery. A dry powder typically contains less than about 15% moisture, preferably less than 11% moisture, and more preferably contains less than about 8% moisture.

As used herein, the term "emitted dose" or "ED" refers to an indication of the delivery of dry powder from a suitable inhaler device after a firing or dispersion event from a powder unit, capsule, or reservoir. ED is defined as the ratio of the dose delivered by an inhaler device to the nominal dose (i.e., the mass of powder per unit dose placed into a suitable inhaler device prior to firing). The ED is an experimentally-determined amount, and is typically determined using an in-vitro device set up which mimics patient dosing. To determine an ED value, a nominal dose of dry powder (as defined above) is placed into a suitable dry powder inhaler, which is then actuated, dispersing the powder. The resulting aerosol cloud is then drawn by vacuum from the device, where it is captured on a tared filter attached to the device mouthpiece. The amount of powder that reaches the filter constitutes the delivered dose. For example, for a 5 mg, dry powder-containing blister pack placed into an inhalation device, if dispersion of the powder results in the recovery of 4 mg of powder on a tared filter as described above, then the ED for the dry powder composition is: 4 mg (delivered dose)/5 mg (nominal dose)×100=80%.

As used herein, the term "geometric diameter" is a measure of geometric particle size and are determined using a Sympatec laser diffraction analyzer.

As used herein, the term "mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by Anderson cascade impaction.

As used herein, the term "pharmaceutically acceptable excipient or carrier" refers to an excipient that can be taken into the lungs in association with an aminoglycoside with no significant adverse toxicological effects to the subject, and particularly to the lungs of the subject.

As used herein, the term "pharmacologically effective amount" or "physiologically effective amount" is the amount of aminoglycoside present in a dry powder composition as described herein that is needed to provide a desired level of drug in the secretions and tissues of the airways and lungs, or alternatively, in the bloodstream of a subject to be treated to give an anticipated physiological response when such composition is administered pulmonarily. The precise amount will depend upon numerous factors, e.g., the particular aminoglycoside, the specific activity of the composition, the delivery device employed, physical characteristics of the powder, its intended use, and resistance of the organisms as well as patient considerations such as severity of the disease state, patient cooperation, etc., and can readily be determined by one skilled in the art, based upon the information provided herein.

As used herein, the term "respiratory infections" includes, but is not limited to upper respiratory tract infections such as sinusitis, pharyngitis, and influenza, and lower respiratory tract infections such as tuberculosis, bronchiectasis (both the cystic fibrosis and non-cystic fibrosis indications), bronchitis (both acute bronchitis and acute exacerbation of chronic bronchitis), and pneumonia (including various types of complications that arise from viral and bacterial infections including hospital-acquired and community-acquired infections).

As used herein, the term "side effects associated with aminoglycoside therapy" refers to undesirable effects suffered by a patient including, but not limited to, ototoxicity and nephrotoxicity and is further intended to include development of resistance to aminoglycoside therapy.

As used herein, the term "therapeutically effective amount" means the amount of aminoglycoside, which when delivered to the lungs and conducting airways of a subject pulmonarily via a dry powder composition as described herein, provides the desired biological effect.

BRIEF DESCRIPTION OF THE DRAWINGS

FIG. 2 depicts a plot of the emitted dose for the tobramycin formulation as a function of capsule fill mass.

FIG. 3 depicts a Plot of the Anderson Cascade Impactor particle size distribution (split flow) for a tobramycin formulation according to this invention.

SUMMARY OF THE INVENTION

Figure 1:
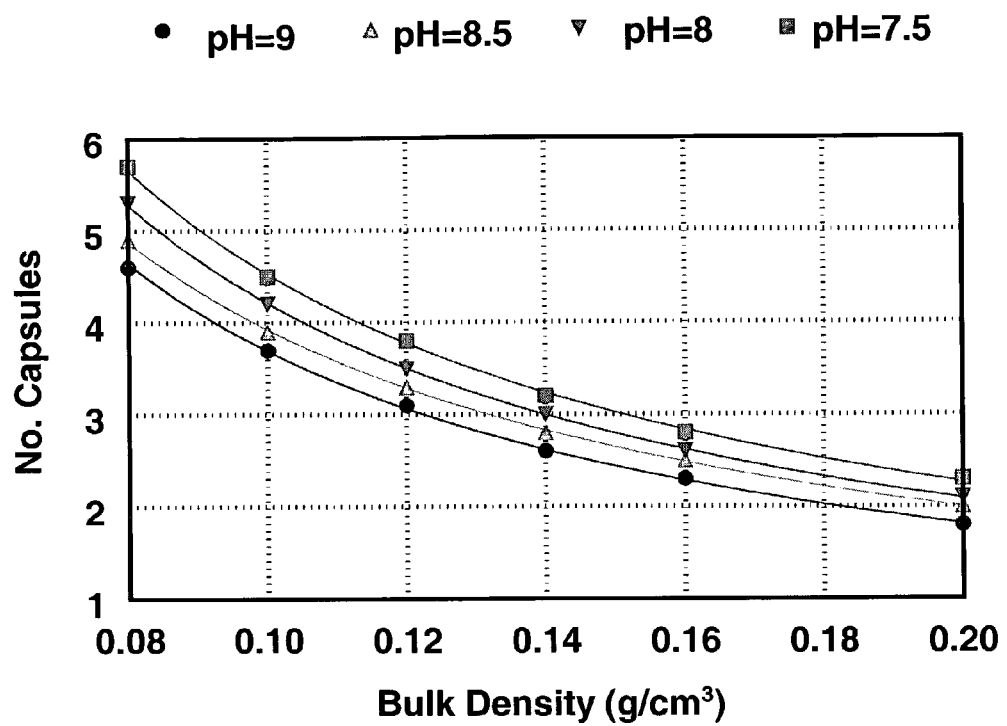
FIG. 1 depicts a plot of the number of capsules required as a function of the bulk density.

It is a general aspect of this invention to provide compositions and methods for the pulmonary administration of aminoglycoside dry powder compositions. The methods of the present invention generally provide much higher localized concentrations of aminoglycosides in the lungs for the treatment of respiratory infections without adverse systemic effects.

Thus, it is an aspect of the present invention to provide compositions and methods for the pulmonary administration of aminoglycosides.

Another aspect of this invention is to provide compositions and methods for the localized administration of aminoglycosides to the lungs for the treatment of respiratory infections.

It is yet another aspect of this invention to provide compositions and methods for pulmonary delivery of aminoglycosides for the treatment of respiratory infections with reduced side effects.

Another aspect of the present invention is directed to methods for administering aminoglycosides with reduced potential for creating resistance to the aminoglycosides.

Another aspect of the invention is directed to the administraiton of tobramycin as a dry powder aerosol wherein the tobramycin formulation is effective to provide a therapeutically effective therapy via administration of less than 5 capsules, preferably less than 4 capsules wherein the capsules are preferably No. 2 capsules.

Yet another aspect of the invention is to provide a reduction in the number of capsules required per dose through increases in powder density, potency, and efficiency of the formulation.

These and other aspects of the present invention will become more fully apparent in view of the following detailed description and examples.

DETAILED DESCRIPTION OF THE INVENTION

According to the present invention, compositions and methods for the pulmonary administration of aminoglycosides for the treatment of respiratory infections are provided. The pulmonary administration route offers a number of benefits, including the potential for achievement of high antibiotic concentrations in respiratory secretions while limiting systemic toxicity. The powders of the present invention exhibit outstanding aerosol characteristics without the need for blending the drug-containing powder with larger carrier particles which help enable the formulations of the present invention meet the high dosage requirements for aminoglycoside therapy with a reduced number of capsules.

Due to the relatively large dosages of aminoglycosides required for therapeutically effective treatment, the dry powder compositions of the present invention are preferably delivered from a pulmonary device at a relatively high emitted dose. According to the invention, the dry powder compositions comprise an emitted dose of at least 50%, more preferably at least 70%, and emitted doses of greater than 80% are most preferred. Such high emitted doses reduce drug costs as more efficient administration of the aminoglycoside is achieved, and also improve patient compliance as fewer device actuations would be needed for effective therapy. The compositions and methods according to this embodiment of the invention provide a significant advance in the pulmonary drug delivery art as large doses of drug are capable of administration pulmonarily to provide a therapeutically effective treatment. Treatments are provided wherein a therapeutically effective amount of aminoglycoside is administered over a 24 hour administration period from a less than 5 unit doses, preferably less than 4 unit doses, in order to provide therapeutically effective therapy.

According to another embodiment of the present invention, administration methods directed at reducing side effects associated with aminoglycoside therapy are provided. These include administration of doses that are much higher than current therapies (e.g. more than 8 times MIC). According to this embodiment, problems associated with underdosing such as development of aminoglycoside resistance as discussed above are reduced. High localized concentrations of aminoglycoside in the lung without adverse side effects associated with aminoglycoside therapy are possible via pulmonary administration of the dry powder compositions of this invention.

According to another embodiment directed at reducing the development of aminoglycoside resistance, two (or perhaps more) antibiotics of different classes acting via different mechanisms are administered in rotation by inhalation.

According to the preferred embodiment, the aminoglycoside dry powder compositions are administered by inhalation via a dry powder inhaler in order to maximize dose convenience and speed of administration.

The aminoglycoside dry powder compositions of this invention generally comprise an aminoglycoside combined with one or more pharmaceutical excipients which are suitable for respiratory and pulmonary administration. Such excipients may serve simply as bulking agents when it is desired to reduce the active agent concentration in the powder which is being delivered to a patient. Such excipients may also serve to improve the dispersibility of the powder within a powder dispersion device in order to provide more efficient and reproducible delivery of the active agent and to improve the handling characteristics of the active agent (e.g., flowability and consistency) to facilitate manufacturing and powder filling. In particular, the excipient materials can often function to improve the physical and chemical stability of the aminoglycoside, to minimize the residual moisture content and hinder moisture uptake, and to enhance particle size, degree of aggregation, surface properties (i.e., rugosity), ease of inhalation, and targeting of the resultant particles to the deep lung. Alternatively, the aminoglycoside may be formulated in an essentially neat form, wherein the composition contains aminoglycoside particles within the requisite size range and substantially free from other biologically active components, pharmaceutical excipients, and the like.

Although administration via DPI is about ten times faster than via nebulizer, it would be highly advantageous from both an economic and compliance standpoint to reduce the total number of capsules needed to provide for an effective therapy via administration from a DPI from 6 to 4 or less, preferably 2 or 3. The following discussion on reducing the number of capsules for an effective aminoglycoside therapy via DPI will focus on a preferred embodiment directed to the administration of tobramycin.

The number of capsules ($n_{capsule}$) required to deliver a certain mass of drug to the lung ($m_{lung}$) can be obtained from the delivery efficiency relationship below:

$$n_{capsule} = \frac{m_{lung}}{m_{capsule} \cdot P \cdot \eta_{lung}} \quad (1)$$

where $m_{capsule}$ is the mass of powder in the capsule, P is the potency of the drug in the drug product (tobramycin free base), $\eta_{lung}$ is the efficiency of aerosol delivery to the lung.

It is clear from this relationship that the total number of capsules required can be reduced by:
 (1) increasing the powder loading in the capsule;
 (2) increasing the potency of drug in powder; and
 (3) increasing the efficiency of aerosol delivery (emitted dose and fine particle dose)

For example, a 35 mg fill, potency of 70%, and an aerosol efficiency of 40%, one needs 2.8 capsules to deliver the 27.6 mg target lung dose. For a 40 mg fill, a potency of 80%, and an efficiency of 50%, one needs just 1.7 capsules. Preferred fill masses according to the invention are within 20-50 mg per capsule. Most preferably 25-40 mg/capsule.

Increasing the fill mass in the capsule can be accomplished by filling a greater percentage of the capsule volume, or by increasing the bulk density of the powder. Formulations according to the present invention have a bulk density of greater than 0.08 g/cm³. Preferred powders according to this invention have a bulk density of 0.10 g/cm³ or greater.

Theoretically, a 50 mg loading would cut the capsule requirements to 3, for a formulation with equivalent potency and aerosol performance to the tobramycin formulation used in the clinical study mentioned above. In order to achieve such a large fill mass in a number 2 capsule the powder density would need to be increased without adversely impacting aerosol characteristics. One of ordinary skill in the art can determine the bulk density at which tobramycin formulations begin to show a drop in aerosol performance in accordance with the teachings herein.

For example, the effect of bulk density on the total number of capsules required is depicted in FIG. 1. FIG. 1 is an estimate of the number of capsules required to deliver 30 mg of the free base to the lung as a function of bulk density and pH. The graph assumes that ⅔ of the capsule volume is filled with powder, that the residual moisture content is 5%, the residual solvent (PFOB) content is 0.1%, and that 40% of the nominal dose is deposited in the lungs.

The potency of tobramycin is determined by a number of factors including the drug loading in the formulation, the percentage of the primary amine groups on the free base that have been reacted with acid to form a salt, the molecular weight of the counterion'(chloride or sulfate), and the residual water and blowing agent trapped in the formulation.

The theoretical potency of free base in the above-mentioned clinical tobramycin formulation was 63%. The balance of mass can be attributed to the sulfate salt, where on average approximately three of the five primary amines were sulfated. The actual potency value for the tobramycin clinical formulation was 53% due to retention of residual moisture (5.3% w/w) and fluorocarbon ($\approx$4.6% w/w) in the formulation.

Figure 4:
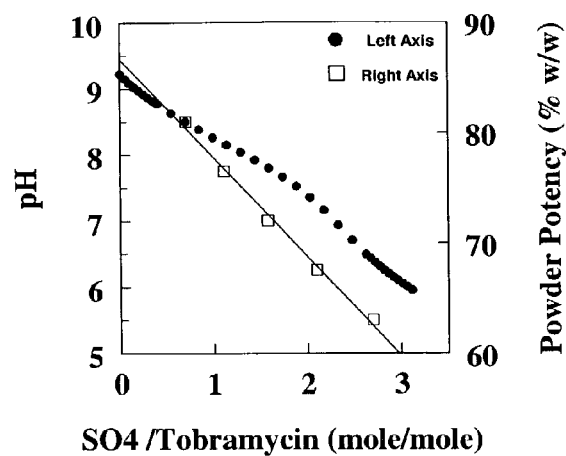
FIG. 4 depicts a titration curve for tobramycin free base with sulfuric acid. The right axis presents the theoretical powder potency for a 90% w/w formulation.

In the TOBI nebulizer product, the pH is titrated to 6.0. Adjusting the pH to 6.0 allows the product to be stable for an extended period without the addition of preservatives such as phenol. Powder formulations will not have the same stability burden, since the time in solution is short. Hence, the sulfate content can be decreased in the final product by titrating the free base to a higher pH than is used in the current TOBI product. According to FIG. 4, increases in potency may be possible from 60% to roughly 80%.

The tobramycin formulation used in the clinical study was comprised of 90% w/w tobramycin sulfate. On average about 3 of the 5 primary amine groups on the free base are sulfated in tobramycin sulfate. From this a molecular weight for tobramycin sulfate can be estimated as follows:

Mol Wt (tobramycin sulfate)=467.54 (free base)+3.1 (96)=765 g/mol

The same calculation can be done for the chloride salt, assuming an equal number of chloride salts per molecule:

Mol Wt (tobramycin chloride)=467.54+3.1(35.5)$\approx$578 g/mol

The potential reduction in the number of capsules afforded by a switch to the chloride salt would be:

(578/765)×6 capsules=4.5 capsules (i.e., a 1.5 capsule savings)

The nature of the acid utilized: sulfuric, hydrochloric, or phosphoric, will depend not only on a desire to reduce the number of capsules, but also on the regulatory impact of changing acid, and the variations in solid state and aerosol performance noted.

Improvements of the aerosol characteristics also contribute to a reduction in the number of capsules necessary for an effective therapy.

Pharmaceutical excipients and additives useful in the present composition include but are not limited to proteins, peptides, amino acids, lipids, polymers, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which may be present singly or in combination. Exemplary protein excipients include serum albumin such as human serum albumin (HSA), recombinant human albumin (rHA), gelatin, casein, and the like. Representative amino acid/polypeptide components, which may also function in a buffering capacity, include alanine, glycine, arginine, betaine, histidine, glutamic acid, aspartic acid, cysteine, lysine, leucine, proline, isoleucine, valine, methionine, phenylalanine, aspartame, and the like. Polyamino acids of the representative amino acids such as di-leucine and tri-leucine are also suitable for use with the present invention. One preferred amino acid is leucine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like.

The dry powder compositions may also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Additionally, the aminoglycoside dry powders of the invention may include polymeric excipients/additives such as polyvinylpyrrolidones, hydroxypropyl methylcellulose, methylcellulose, ethylcellulose, Ficolls (a polymeric sugar), dextran, dextrates (e.g., cyclodextrins, such as 2-hydroxypropyl-β-cyclodextrin, hydroxyethyl starch), polyethylene glycols, pectin, flavoring agents, salts (e.g. sodium chloride), antimicrobial agents, sweeteners, antioxidants, antistatic agents, surfactants (e.g., polysorhates such as "TWEEN 20" and "TWEEN 80", lecithin, oleic acid, benzalkonium chloride, and sorbitan esters), lipids (e.g., phospholipids, fatty acids), steroids (e.g., cholesterol), and chelating agents (e.g., EDTA). Other pharmaceutical excipients and/or additives suitable for use in the aminoglycoside compositions according to the invention are listed in "Remington: The Science & Practice of Pharmacy", 19th ed., Williams & Williams, (1995), and in the "Physician's Desk Reference", $52^{nd}$ ed., Medical Economics, Montvale, N.J. (1998), the disclosures of which are herein incorporated by reference.

According to the present invention, a dispersing agent for improving the intrinsic dispersibility properties of the aminoglycoside powders is added. Suitable agents are disclosed in PCT applications WO 95/31479, WO 96/32096, and WO 96/32149, hereby incorporated in their entirety by reference. As described therein, suitable agents include water soluble polypeptides and hydrophobic amino acids such as tryptophan, leucine, phenylalanine, and glycine. Leucine and trileucine are particularly preferred for use according to this invention.

In accordance with the invention, the solid state matrix formed by the aminoglycoside and excipient imparts a stabilizing environment to the aminoglycoside. The stabilizing matrix may be crystalline, an amorphous glass, or a mixture of both forms. Most suitable are dry powder formulations which are a mixture of both forms. For aminoglycoside dry powder formulations which are substantially amorphous, preferred are those formulations exhibiting glass transition temperatures ($T_g$) above about 35° C., preferably above about 45° C., and more preferably above about 55° C. Preferably, $T_g$ is at least 20° C. above the storage temperature. According to a preferred embodiment, the aminoglycoside formulations comprise a phospholipid as the solid state matrix as disclosed in WO 99/16419 and WO 01/85136, hereby incorporated in their entirety by reference.

The aminoglycoside contained in the dry powder formulations is present in a quantity sufficient to form a pharmacologically-effective amount when administered by inhalation to the lung. The dry powders of the invention will generally contain from about 20% by weight to about 100% by weight aminoglycoside, more typically from about 50% to 99% by weight aminoglycoside, and preferably from about 80 to 95% by weight aminoglycoside. Correspondingly, the amount of excipient material(s) will range up to about 80% by weight, more typically up to about 50% by weight, and preferably from about 20 to 5% by weight.

In one preferred embodiment of the invention, the dry powder contains at least 80% by weight aminoglycoside in order to provide a unit dose effective to administer up to 100 mg, preferably from 10-60 mg/unit dose with the appropriate dose adjusted for the particular aminoglycoside as readily determined by one of ordinary skill.

Preparation of Aminoglycoside Dry Powders

Dry powder aminoglycoside formulations may be prepared by spray drying under conditions which result in a substantially amorphous glassy or a substantially crystalline bioactive powder as described above. Spray drying of the aminoglycoside-solution formulations is carried out, for example, as described generally in the "Spray Drying Handbook", $5^{th}$ ed., K. Masters, John Wiley & Sons, Inc., NY, N.Y. (1991), and in WO 97/41833, the contents of which are incorporated herein by reference.

To prepare an aminoglycoside solution for spray drying according to one embodiment of the invention, an aminoglycoside is generally dissolved in a physiologically acceptable solvent such as water. The pH range of solutions to be spray-dried is generally maintained between about 3 and 10, preferably 5 to 8, with near neutral pHs being preferred, since such pHs may aid in maintaining the physiological compatibility of the powder after dissolution of powder within the lung. The aqueous formulation may optionally contain additional water-miscible solvents, such as alcohols, acetone, and the like. Representative alcohols are lower alcohols such as methanol, ethanol, propanol, isopropanol, and the like. Aminoglycoside solutions will generally contain aminoglycoside dissolved at a concentration from 0.05% (weight/volume) to about 20% (weight/volume), usually from 0.4% to 5.0% (weight/volume).

The aminoglycoside-containing solutions are then spray dried in a conventional spray drier, such as those available from commercial suppliers such as Niro A/S (Denmark), Buchi (Switzerland) and the like, resulting in a stable, aminoglycoside dry powder. Optimal conditions for spray drying the aminoglycoside solutions will vary depending upon the formulation components, and are generally determined experimentally. The gas used to spray dry the material is typically air, although inert gases such as nitrogen or argon are also suitable. Moreover, the temperature of both the inlet and outlet of the gas used to dry the sprayed material is such that it does not cause deactivation of aminoglycoside in the sprayed material. Such temperatures are typically determined experimentally, although generally, the inlet temperature will range from about 50° C. to about 200° C. while the outlet temperature will range from about 30° C. to about 150° C.

Alternatively, aminoglycoside dry powders may be prepared by lyophilization, vacuum drying, spray freeze drying, super critical fluid processing, or other forms of evaporative drying or by blending, grinding or jet milling formulation components in dry powder form. In some instances, it may be desirable to provide the aminoglycoside dry powder formulation in a form that possesses improved handling/processing characteristics, e.g., reduced static, better flowability, low caking, and the like, by preparing compositions composed of fine particle aggregates, that is, aggregates or agglomerates of the above-described aminoglycoside dry powder particles, where the aggregates are readily broken back down to the fine powder components for pulmonary delivery, as described, e.g., in U.S. Pat. No. 5,654,007, incorporated herein by reference. Alternatively, the aminoglycoside powders may be prepared by agglomerating the powder components, sieving the materials to obtain the agglomerates, spheronizing to provide a more spherical agglomerate, and sizing to obtain a uniformly-sized product, as described, e.g., in WO 95/09616, incorporated herein by reference. The aminoglycoside dry powders are preferably maintained under dry (i.e., relatively low humidity) conditions during manufacture, processing, and storage.

According to a preferred embodiment, the aminoglycoside powders are made according to the emulsification/spray drying process disclosed in WO 99/16419 and WO 01/85136 cited above. Formulations according to such preferred embodiments are engineered to comprise dry powder particulates comprising at least 75% w/w, preferably at least 85% w/w tobramycin, 2-25% w/w of a phospholipid, preferably 8-18% w/w, and 0-5% w/w of a metal ion such as calcium chloride. The particulates comprise a geometric diameter of less than 5 microns, an MMAD of less than 5 microns, preferably 1-4 microns, and a bulk density of greater than 0.08 g/cm$^3$, preferably greater than 0.12 g/cm$^3$.

Aminoglycoside Dry Powder Characteristics

It has been found that certain physical characteristics of the aminoglycoside dry powders, to be described more fully below, are important in maximizing the efficiency of aerosolized delivery of such powders to the lung.

The aminoglycoside dry powders are composed of particles effective to penetrate into the lungs, that is, having a geometric diameter of less than about 10 μm, preferably less than 7.5 μm, and most preferably less than 5 μm, and usually being in the range of 0.1 μm to 5 μm in diameter. Preferred powders are composed of particles having a geometric diameter from about 0.5 to 4.0 μm.

The aminoglycoside powders of the invention are further characterized by an aerosol particle size distribution less than about 10 μm mass median aerodynamic diameter (MMAD), and preferably less than 5.0 μm. The mass median aerodynamic diameters of the powders will characteristically range from about 0.5-10 preferably from about 0.5-5.0 μm MMAD, more preferably from about 1.0-4.0 μm MMAD. To further illustrate the ability to prepare aminoglycoside powders having an aerosol particle size distribution within a range suitable for pulmonary administration, exemplary aminoglycoside dry powders are composed of particles having an aerosol particle size distribution less than about 5 μm MMAD, and more specifically, characterized by MMAD values less than 4.0 μm.

The aminoglycoside dry powders generally have a moisture content below about 15% by weight, usually below about 11% by weight, and preferably below about 8% by weight. The moisture content of representative aminoglycoside dry powders prepared as described herein is provided in the Examples.

The emitted dose (ED) of these powders is greater than 50%. More preferably, the ED of the aminoglycoside powders of the invention is greater than 70%, and is often greater than 80%. In looking at the Examples, it can be seen that applicants have successfully prepared a large number of representative aminoglycoside dry powders with ED values greater than or equal to 80%.

Pulmonary Administration

The aminoglycoside dry powder formulations described herein may be delivered using any suitable dry powder inhaler (DPI), i.e., an inhaler device that utilizes the patient's inhaled breath as a vehicle to transport the dry powder drug to the lungs. Preferred dry powder inhalation devices are described in U.S. Pat. Nos. 5,458,135; 5,740,794; 5,775,320; and 5,785,049, and in copending U.S. application Ser. Nos. 09/004,558 filed Jan. 8, 1998, Ser. No. 09/312,434 filed Jun. 4, 1999, 60/136,518 filed May 28, 1999, and 60/141,793 filed Jun. 30, 1999, listed above. When administered using a device of this type, the powdered medicament is contained in a receptacle having a puncturable lid or other access surface, preferably a blister package or cartridge, where the receptacle may contain a single dosage unit or multiple dosage units. Convenient methods for filling large numbers of cavities with metered doses of dry powder medicament are described in U.S. Pat. No. 5,826,633, incorporated herein by reference.

Also suitable for delivering the aminoglycoside powders described herein are dry powder inhalers of the type described, for example, in U.S. Pat. Nos. 3,906,950 and 4,013,075, 4,069,819, and 4,995,385, incorporated herein by reference, wherein a premeasured dose of aminoglycoside dry powder for delivery to a subject is contained within a capsule such as a hard gelatin capsule or HPMC capsule. HPMC capsules are preferred, preferably size #2 capsules containing up to 50 mg powder, preferably 20-40 mg. It is to be understood that other sized capsules, such as 00, 0, No. 1, or No. 3 sized capsules are also suitable for use with the present invention and their suitability depends, among other factors, upon the inhalation device used to administer the powders.

Other dry powder dispersion devices for pulmonarily administering aminoglycoside dry powders include those described, for example, in EP 129985; EP 472598; EP 467172; and U.S. Pat. No. 5,522,385, incorporated herein in their entirety by reference. Also suitable for delivering the aminoglycoside dry powders of the invention are inhalation devices such as the Astra-Draco "TURBUHALER". This type of device is described in detail in U.S. Pat. Nos. 4,668,218; 4,667,668; and 4,805,811, all of which are incorporated herein by reference.

Also suitable are devices which employ the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device, such as described in U.S. Pat. No. 5,388,572, incorporated herein by reference.

Prior to use, the aminoglycoside dry powders are generally stored in a receptacle under ambient conditions, and preferably are stored at temperatures at or below about 30° C., and relative humidities (RH) ranging from about 30 to 60%. More preferred relative humidity conditions, e.g., less than about 30%, may be achieved by the incorporation of a dessicating agent in the secondary packaging of the dosage form.

The following examples are offered by way of illustration, not by way of limitation. The following materials were used in the Examples (the grades and manufacturers are representative of many that are suitable):

Gentamicin Sulfate (II&A (Canada) Industrial)

Netilmicin Sulfate (Scientific Instruments And Technology)

Tobramycin (Chiron, Berkeley, Calif.)

L-Leucine (Aldrich)

Hydrochloric Acid (J. T. Baker)

Sodium Hydroxide 0.1N Volumetric Solution (J. T. Baker)

Ethanol, 200 proof (USP/NF, Spectrum Chemical Mfg. Corp.)

Methanol (HPLC grade, EM Industries)

EXAMPLE 1

A. Formulation

Dry powder compositions containing gentamicin were prepared by mixing gentamicin sulfate and excipient(s) (if used)

with a liquid medium to form a solution. The pH of the solution was adjusted as appropriate to facilitate solubilization and/or stabilization of the components in the solution. Quantitative formulations are identified in Table 1 below.

B. Spray Drying

The gentamicin solutions were spray dried on Buchi 190 Mini Spray Dryers, with nozzles and cyclones that were designed to generate and catch very fine particles. For formulations that utilized organic solvents, a modified Buchi 190 Mini Spray Dryer was used that was supplied with nitrogen as the gas source and equipped with an oxygen sensor and other safety equipment to minimize the possibility of explosion. The solution feed rate was 5 ml/minute, solution was maintained at room temperature, inlet temperature range was 120-131° C. and was adjusted to obtain an outlet temperature of approximately 80° C., the drying gas flow rate was about 18 SCFM, and the atomizing air was supplied at 0.5 to 1.5 SCFM, typically at a pressure of about 100 PSI.

C. Characterization

Each powder was characterized in terms of moisture content, emitted dose (ED), and mass median aerodynamic diameter (MMAD). ED is a measure of efficiency for the powder package/device combination. MMAD refers to a measure of the particle size of the aerosolized powder.

Moisture content was determined by the Karl-Fischer Reagent titrimetric method or by thermogravimetric analysis as indicated in the following tables.

Morphology was determined by scanning electron microscopy (SEM).

To determine the ED, the spray dried powders were first filled into blister packs. The test was performed by connecting a vacuum system to the mouthpiece of an inhaler device of the type describe in U.S. Pat. No. 5,740,794 identified above. The vacuum system was set to be similar to a human inhalation with regard to volume and flow rate (1.2 liters total at 30 liters/minute). A blister package containing 5 mg of the formulation to be evaluated was loaded into a device, which was held in a testing fixture. The device was pumped and fired, and the vacuum "inhalation" switched on. The aerosol cloud was drawn out of the device chamber by the vacuum, and the powder was collected on a filter placed between the mouthpiece and the vacuum source. The weight of the powder collected on the filter was determined. Emitted dose was calculated as this weight, multiplied by one hundred, divided by the fill weight in the blister. A higher number is a better result than a lower number.

MMAD was determined with an Andersen cascade impactor. In a cascade impactor the aerosolized powder (which was aerosolized using an inhaler device as described in U.S. Pat. No. 5,740,794) enters the impactor via an air stream, and encounters a series of stages that separate particles by their aerodynamic diameter (the smallest particles pass farthest down the impactor). The amount of powder collected on each stage was determined gravimetrically, and the mass median aerodynamic diameter was then calculated.

Tables 1 show the quantitative composition of gentamicin formulations, a description of the particle morphology, moisture content, MMAD, and emitted dose of the resultant gentamicin powders.

TABLE 1

Gentamicin Dry Powder Compositions

| Batch Number | Quantitative Composition | | Particle Morphology | Moisture Content | MMAD (μm) | Emitted Dose |
|---|---|---|---|---|---|---|
| 1326-31 | Gentamicin sulfate<br>DI water<br>Hydrochloric acid | 2076 mg<br>200 ml<br>QS to<br>pH = 5 | Smooth spheres sometimes with a large dimple or two | 4.1%[1] | 3.0 | 37% (RSD[3] = 6) |
| 1326-32 | Gentamicin sulfate<br>DI water<br>Sodium hydroxide | 2053 mg<br>200 ml<br>QS to<br>pH = 10 | Slightly dimpled spheres | 1.1%[1] | 2.4 | 40% (RSD = 14) |
| 1300-MG-11 | Gentamicin sulfate<br>Ethanol<br>DI water | 2012 mg<br>40 ml<br>160 ml | Smooth spheres sometimes with a large dimple or two | 4.8%[2] | 3.0 | 45% (RSD = 10) |
| 1300-MG-12 | Gentamicin sulfate<br>L-leucine<br>DI water | 2006 mg<br>205 mg<br>220 ml | Highly dimpled spheres | 6.2%[2] | 2.6 | 61% (RSD = 7) |
| 1300-MG-18 | Gentamicin sulfate<br>L-leucine<br>DI water | 1500 mg<br>510 mg<br>200 ml | Raisin-like | 4.3%[2] | 2.4 | 80% (RSD = 6) |

[1]Determined with Karl-Fischer reagent titrimetric method
[2]Determined with thermogravimetric analysis
[3]Relative Standard Deviation

EXAMPLE 2

Formulations containing netilmicin were prepared according to the procedure set forth in Example 1. The netilmicin formulations were spray dried and characterized as set forth in Example 1. Results are set forth in Table 2 below.

TABLE 2

Netilmicin Dry Powder Compositions

| Batch Number | Quantitative Composition | | Particle Morphology | Moisture Content[1] | MMAD (μm) | Emitted Dose |
|---|---|---|---|---|---|---|
| 1300-MG-9 | Netilmicin Sulfate | 1626 mg | Irregular and jagged | 4.2% | 3.2 | 47% (RSD = 8) |
|  | DI water | 163 ml |  |  |  |  |
| 1300-MG-14 | Netilmicin Sulfate | 1512 mg | Smooth spheres often with a single or a few large dimples | 5.1% | 2.9 | 39% (RSD = 7) |
|  | Ethanol | 30 ml |  |  |  |  |
|  | DI water | 120 ml |  |  |  |  |
| 1300-MG-15 | Netilmicin Sulfate | 1202 mg | Raisin-like | 4.1% | 2.3 | 78% (RSD = 10) |
|  | L-leucine | 393 mg |  |  |  |  |
|  | DI water | 160 ml |  |  |  |  |
| 1300-MG-19 | Netilmicin Sulfate | 1426 mg | Dimpled Spheres | 5.3% | 2.6 | 75% (RSD = 6) |
|  | L-leucine | 77 mg |  |  |  |  |
|  | DI water | 150 ml |  |  |  |  |

[1]Determined with thermogravimetric analysis

EXAMPLE 3

The procedures set forth in Example 1 were repeated for the aminoglycoside tobramycin. Results are represented in Table 3 below.

TABLE 3

Tobramycin Dry Powder Compositions

| Batch Number | Quantitative Composition | | Particle Morphology | Moisture Content[1] | MMAD (μm) | Emitted Dose |
|---|---|---|---|---|---|---|
| 1504-HS-7 | Tobramycin | 2.04 g | Not available | 3.9% | 2.3 | 32% (RSD = 8) |
|  | DI water | 204 ml |  |  |  |  |
| 1504-HS-9 | Tobramycin | 1.50 g | Dimpled spheres | 2.6% | 2.3 | 72% (RSD = 5) |
|  | L-Leucine | 0.51 g |  |  |  |  |
|  | DI water | 200 ml |  |  |  |  |
| 1504-HS-39 | Tobramycin | 1.50 g | Dimpled spheres | 5.4% | 2.4 | 73% (RSD = 5) |
|  | L-Leucine | 0.51 g |  |  |  |  |
|  | DI water | 200 ml |  |  |  |  |
|  | Sulfuric acid to adjust solution | to pH = 5.5 |  |  |  |  |

[1]Determined with thermogravimetric analysis

EXAMPLE 2

Powder Manufacture

Tobramycin sulfate formulations set forth in Table 4 below was manufactured according to the following procedure. SWFI was heated above the gel to liquid crystal temperature of disteroyl phosphatidylcholine (DSPC) (≈80° C.). DSPC and calcium chloride dihydrate were then added to the heated water. The resulting lipid dispersion was mixed in an UltraTurrax T-50 (IKA Labortechnik) at 8,000 rpm for 5 min. Perfluorooctyl bromide (PFOB) was then added dropwise (15 ml min$^{-1}$) to the lipid dispersion under mixing. After the addition was complete the resulting PFOB-in-water emulsion was mixed for an additional 10 min at 10,000 rpm. Emulsification in the UltraTurrax produces droplets in the micron-size range. Tobramycin sulfate was then dissolved in the continuous phase of the emulsion and the resulting dispersion was used as the feedstock for spray drying.

The feedstock was then spray dried using the equipment and conditions set forth in Table 5 below.

TABLE 4

Tobramycin Sulfate Formulation.

| | |
|---|---|
| Tobramycin Sulfate | 90.04% w/w |
| DSPC | 9.56% w/w |
| CaCl$_2$ | 0.40% w/w |
| PFOB, φ | 0.198 v/v |
| PFOB/Total Solids | 6.37% w/w |
| Feed Concentration | 5.92% w/v |

TABLE 5

Spray drying Equipment and Conditions.

| | Lot # | | |
|---|---|---|---|
|  | 2715-08 | 2792-11 | 2792-12 |
| Spray Dryer: | Buchi | NIRO | NIRO |
| Drying Gas | CDA | Room Air | Room Air |
| Gauge Conditions: |  |  |  |
| Total Air Flow (SCFM) | 12 | 70 | 70 |
| Inlet Temperature (° C.) | 85 | 140 | 112 |

TABLE 5-continued

Spray drying Equipment and Conditions.

| | Lot # | | |
|---|---|---|---|
| | 2715-08 | 2792-11 | 2792-12 |
| Outlet Temperature (° C.) | 62 | 76 | 54 |
| Pump Rate (mL/min) | 2.1 | 35 | 35 |
| Atomizer Pressure (psi) | 11 | 100 | 100 |
| Atomizer Flow Rate (SCFM) | 2.8 | 12 | 12 |

Hand-Filling: The powder was hand filled into #2 HPMC capsules for aerosol testing. Capsules were allowed to equilibrate at <5% RH overnight. Powders were placed into a capsule filling station with relative humidity of 10 to 15% and allowed to equilibrate for 10 minutes prior to handling. Fill weights ranging from 20 mg to 40 mg were explored, representing fill volumes of approximately ½ to ⅞. Aerosol testing was performed using a Turbospin® (PH&T, Italy) capsule based passive delivery device. The filled capsules were tested the day of filling.

Particle Size Analysis by Laser Diffraction: The geometric particle size analysis of the powders were determined using a Sympatec laser diffraction analyzer (HELOS H1006, Clausthal-Zellerfeld, Germany) equipped with a RODOS type T4.1 vibrating trough. Approximately 2 mg of bulk powder was emptied onto the RODOS vibrating trough, which was subsequently atomized through a laser beam using 1 bar of air pressure, 53 mbar of vacuum, 70% feed rate, 1.30 mm funnel gap with the R2 lens setting. Data was collected over an interval of 0.4 s, with a 175 μm focal length, triggered at 0.1% obscuration. Particle size distributions were determined using the Fraünhofer model.

Residual Moisture: The residual moisture in the bulk powder was determined by Karl Fisher titrimetry.

The Emitted Dose Testing: This measurement was performed using the medium resistance Turbospin device operated at its optimal sampling flow rate of 60 L·min$^{-1}$. A total of 10 measurements was determined for each fill mass explored. Results are depicted in FIG. 2, which shows emitted dose results for the same formulation at fill masses as high as 40 mg. No significant decreases in ED or increases in RSD are noted. Increasing the powder load by 25% to 35% (with equivalent aerosol performance) results in a capsule savings of about 2 capsules, dropping the capsule needs from 6 to 4.

Aerodynamic Particle Size Distribution: Aerodynamic particle size distributions were determined gravimetrically on an Andersen cascade impactor (ACI). Particle size distributions were measured at a flow rates 56.6 L·min$^{-1}$ (i.e., forceful inhalation effort) using the Turbospin DPI device. Results are depicted in FIG. 3, which shows a plot of the aerosol particle size distribution as a function of a capsule fill mass. It is clear that a significant increase in capsule fill mass is achievable without significant variations in the aerodynamic particle size distribution.

The invention claimed is:

1. A respirable unit dose of a dispersible powder composition, the composition comprising particles comprising an aminoglycoside and a phospholipid for delivery to the lungs by inhalation, wherein the particles have a geometric diameter of less than 5 microns, wherein the respirable unit dose comprises a fill mass of between 25 and 50 mg and said fill mass comprises between about 14-35 mg of aminoglycoside or salt thereof.

2. A respirable unit dose according to claim 1 wherein the composition is effective to provide a therapeutically effective therapy via administration of less than 6 respirable unit doses.

3. A respirable unit dose according to claim 1 wherein the composition comprises from about 50% to about 99% by weight aminoglycoside.

4. A respirable unit dose according to claim 1 wherein the particles further comprise calcium chloride.

5. A respirable unit dose according to claim 1 wherein the respirable unit dose is provided in a capsule, the capsule comprising hydroxypropylmethylcellulose.

6. A respirable unit dose according to claim 1 wherein the particles have a bulk density of between 0.08 and 0.20 g/cm$^3$.

7. A respirable unit dose according to claim 1 wherein the particles have a mass median aerodynamic diameter less than 5 microns.

8. A respirable unit dose according to claim 1 wherein the composition has a pH of between 7 and 10.

9. A respirable unit dose according to claim 1 wherein the respirable unit dose comprises a volume equivalent to a size #00 capsule or smaller capsule size.

10. A respirable unit dose according to claim 1 wherein the respirable unit dose comprises a volume equivalent to a size #2 capsule or smaller capsule size.

11. A respirable unit dose according to claim 1 wherein the aminoglycoside comprises one or more of gentamicin, netilmicin, paramecin, tobramycin, amikacin, kanamycin, neomycin, and streptomycin.

12. A respirable unit dose according to claim 1 wherein the aminoglycoside comprises tobramycin or salt thereof.

13. A respirable unit dose according to claim 1 wherein the particles are spray dried particles.

14. A respirable unit dose according to claim 1 wherein the particles have a moisture content of less than 15% by weight.

15. A respirable unit dose according to claim 1 wherein the particles are hollow and/or porous.

16. A respirable unit dose according to claim 1 wherein each respirable unit dose comprises an emitted dose greater than 70%.

17. A method for administering a composition, the method comprising administering by inhalation less than 6 respirable unit doses according to claim 1 to provide at least 27.6 mg of aminoglycoside to the lungs.

18. A method for treating cystic fibrosis, the method comprising administering a pharmacologically effective amount of aminoglycoside comprising tobramycin to the lungs from a respirable unit dose according to claim 1.

19. A method for administering aminoglycoside to reduce the potential for development of bacteria in the lungs, the method comprising administering a pharmacologically effective amount of aminoglycoside to the lungs from a respirable unit dose according to claim 1.

* * * * *